United States Patent
List et al.

(10) Patent No.: US 10,071,094 B2
(45) Date of Patent: Sep. 11, 2018

(54) PROTEIN PHOSPHATASE 2A INHIBITORS FOR TREATING MYELODYSPLASTIC SYNDROMES

(71) Applicants: H. Lee Moffitt Cancer Center and Research Institute, Inc., Tampa, FL (US); Lixte Biotechnology, Inc., East Setauket, NY (US)

(72) Inventors: Alan F. List, Tampa, FL (US); David A. Sallman, Tampa, FL (US); John S. Kovach, East Setauket, NY (US)

( * ) Notice: Subject to any disclaimer, the term of this patent is extended or adjusted under 35 U.S.C. 154(b) by 0 days.

(21) Appl. No.: 15/328,235

(22) PCT Filed: Jul. 23, 2015

(86) PCT No.: PCT/US2015/041714
§ 371 (c)(1),
(2) Date: Jun. 29, 2017

(87) PCT Pub. No.: WO2016/014783
PCT Pub. Date: Jan. 28, 2016

(65) Prior Publication Data
US 2017/0340628 A1 Nov. 30, 2017

Related U.S. Application Data

(60) Provisional application No. 62/029,327, filed on Jul. 25, 2014, provisional application No. 62/028,729, filed on Jul. 24, 2014.

(51) Int. Cl.
| | | |
|---|---|---|
| *A61K 31/535* | (2006.01) | |
| *A61K 31/496* | (2006.01) | |
| *A61K 31/34* | (2006.01) | |
| *A61K 31/454* | (2006.01) | |
| *A61K 31/573* | (2006.01) | |
| *A61K 31/706* | (2006.01) | |
| *A61K 47/18* | (2017.01) | |

(52) U.S. Cl.
CPC ............ *A61K 31/496* (2013.01); *A61K 31/34* (2013.01); *A61K 31/454* (2013.01); *A61K 31/573* (2013.01); *A61K 31/706* (2013.01); *A61K 47/183* (2013.01)

(58) Field of Classification Search
CPC ........................... C07D 405/12; A61K 31/495
USPC ...................................................... 514/231.5
See application file for complete search history.

(56) References Cited

U.S. PATENT DOCUMENTS

| | | | |
|---|---|---|---|
| 7,998,957 | B2 | 8/2011 | Kovach et al. |
| 8,058,268 | B2 | 11/2011 | Kovach |
| 8,143,445 | B2 | 3/2012 | Kovach et al. |
| 8,227,473 | B2 | 7/2012 | Kovach et al. |
| 8,329,719 | B2 | 12/2012 | Kovach |
| 8,426,444 | B2 | 4/2013 | Kovach et al. |
| 8,541,458 | B2 | 9/2013 | Kovach et al. |
| 8,822,461 | B2 | 9/2014 | Kovach et al. |
| 9,079,917 | B2 | 7/2015 | Kovach et al. |
| 9,526,915 | B2 | 12/2016 | Kovach |
| 9,833,450 | B2 | 12/2017 | Kovach et al. |
| 2008/0267947 | A1 | 10/2008 | Cirrito et al. |
| 2010/0029683 | A1 | 2/2010 | Kovach et al. |
| 2012/0135522 | A1 | 5/2012 | Kovach et al. |
| 2012/0316081 | A1 | 12/2012 | List et al. |
| 2014/0235649 | A1 | 8/2014 | Kovach et al. |
| 2015/0148353 | A1 | 5/2015 | Kovach |
| 2015/0174123 | A1 | 6/2015 | Kovach |
| 2016/0051544 | A1 | 2/2016 | Kovach et al. |
| 2016/0074390 | A1 | 3/2016 | Kovach et al. |
| 2016/0264593 | A1 | 9/2016 | Kovach et al. |
| 2016/0333024 | A1 | 11/2016 | Kovach et al. |
| 2017/0136008 | A1 | 5/2017 | Kovach et al. |
| 2017/0209434 | A1 | 7/2017 | List et al. |
| 2017/0259081 | A1 | 9/2017 | Kovach et al. |
| 2017/0305925 | A1 | 10/2017 | Piotrowski et al. |
| 2017/0369503 | A1 | 12/2017 | Kovach et al. |

FOREIGN PATENT DOCUMENTS

| | | | |
|---|---|---|---|
| WO | WO 2006/052842 A2 | 5/2006 | |
| WO | 2007092414 A1 | 8/2007 | |
| WO | 2008097561 A1 | 8/2008 | |
| WO | 2009020565 A1 | 2/2009 | |
| WO | 2010014141 A1 | 2/2010 | |
| WO | 2010014254 A1 | 2/2010 | |
| WO | 2010147612 A1 | 12/2010 | |
| WO | WO 2011/143147 A1 | 11/2011 | |
| WO | 2012162535 A1 | 11/2012 | |
| WO | 2013056211 A2 | 4/2013 | |
| WO | 2014005080 A1 | 1/2014 | |
| WO | 2014005084 A1 | 1/2014 | |
| WO | WO 2014/089279 A1 | 6/2014 | |
| WO | 2014137741 A1 | 9/2014 | |
| WO | 2014149494 A1 | 9/2014 | |
| WO | 2014168941 A1 | 10/2014 | |
| WO | 2015073802 A1 | 5/2015 | |
| WO | 2016014778 A1 | 1/2016 | |
| WO | 2016134257 A1 | 8/2016 | |

OTHER PUBLICATIONS

International Search Report in connection with PCT International Application No. PCT/US2015/041714.
Written Opinion of the International Searching Authority in connection with PCT International Application No. PCT/US2015/041714.
S. Wei, et al.; "A critical role for phosphatase haplodeficiency in the selective suppression of deletion 5q MDS by lenalidomide"; Proc Natl Acad Sci USA; 106:12974-12979; May 26, 2009.

(Continued)

*Primary Examiner* — Raymond J Henley, III
(74) *Attorney, Agent, or Firm* — Andrea L. C. Reid; Dechert LLP

(57) ABSTRACT

Disclosed are methods for treating a myelodysplastic syndrome (MDS) in a subject that involves administering to the subject a therapeutically effective amount of a protein phosphatase 2A (PP2A) inhibitor.

19 Claims, 7 Drawing Sheets

(56) References Cited

OTHER PUBLICATIONS

Bai et al., Inhibition of protein phosphatase 2A enhances cytotoxicity and accessibility of chemotherapeutic drugs to hepatocellular carcinomas, Author Manuscript Published OnlineFirst on May 27, 2014; DOI: 10.1158/1535-7163. MCT-13-0800.
Durusu et al., "Anti-cancer effect of clofazimine as a single agent and in combination with cisplatin on U266 multiple myelma cell line," Leukemia Research, vol. 55, No Month Listed 2007 (33-40).
Greenberg et al., "International scoring system for evaluating prognosis in myelodysplastic syndromes," Blood, vol. 89, No. 6, Mar. 1997 (pp. 2079-2088).
Greenberg et al., "Revised international prognostic scoring system for myelodysplastic syndromes," Blood, vol. 120, No. 12, Sep. 2012 (pp. 2454-2465).
International Preliminary Report on Patentability issued in Application No. PCT/US2015/041709, dated Feb. 2, 2017.
International Preliminary Report on Patentability issued in Application No. PCT/US2015/041714, dated Feb. 2, 2017.
International Search Report and Written Opinion issued in Application No. PCT/US2015/041709, dated Oct. 23, 2015.
International Search Report and Written Opinion issued in Application No. PCT/US2015/041714, dated Oct. 30, 2015.
Komrokji et al., "Role of Lenalidomide in the Treatment of Myelodysplastic Syndromes", Seminars in Oncology 2011, 38, 5, 648-657.
List et al., "Efficacy of Lenalidomide in Myelodysplastic Syndromes", N Engl J Med 2005, 352, 549-557.
List et al., "Lenalidomide in the Myelodysplastic Syndrome with Chromosome 5q Deletion," N Engl J Med 2006, 355, 1456-1465.
McDaniel, "Lenalidomide targets the T-cell co-stimulatory pathway to mediate immune modulation," Graduate Thesis and Dissertation, University of South Florida, Scholar Commons, Jan. 2012 (191 pgs.).
McDaniel et al., "Reversal of T-cell Tolerance in Myelodysplastic Syndrome through Lenalidomide Immune Modulation," Leukemia, vol. 26, No. 6, Jun. 2012 (pp. 1425-1429).
Padron, et al., "The 5q- Syndrome: Biology and Treatment," Current Treatment Options in Oncology, vol. 12, 2011 (pp. 354-368).
Sallman et al., "PP2A: the Achilles heel in MDS with 5q deletion", Frontiers in Oncology 2014, vol. 4, Art. 264, 1-7.
S. Wei, et al.; Correction for "A critical role for phosphatase haplodeficiency in the selective suppression of deletion 5q MDS by lenalidomide," (which appeared in issue 31, Aug. 4, 2009, of Proc Natl Acad Sci USA, 106:12974-12979; first published May 26, 2009, 10.1073/pnas.0811267106) Proc Natl Acad Sci USA, 110(35):14504 , Aug. 27, 2013.
U.S. Appl. No. 15/809,439 of Kovach et al., filed Nov. 10, 2017.
U.S. Appl. No. 15/816,372 of Kovach et al., filed Nov. 17, 2017.

PROTEIN PHOSPHATASE 2A INHIBITORS FOR TREATING MYELODYSPLASTIC SYNDROMES

CROSS-REFERENCE TO RELATED APPLICATIONS

This application is a § 371 national stage of PCT International Application No. PCT/US2015/041714, filed Jul. 23, 2015, claiming the benefit of U.S. Provisional Applications Nos. 62/029,327, filed Jul. 25, 2014, and 62/028,729, filed Jul. 24, 2014, the contents of each of which are hereby incorporated by reference in its entirety.

BACKGROUND

Myelodysplastic syndromes (MDS) are hematopoietic stem cell malignancies with a rising prevalence owing to the aging of the American population. MDS comprise a group of malignant hematologic disorders associated with impaired erythropoiesis, dysregulated myeloid differentiation and increased risk for acute myeloid leukemia (AML) transformation. The incidence of MDS is increasing with 15,000 to 20,000 new cases each year in the United States and large numbers of patients requiring chronic blood transfusions. Ineffective erythropoiesis remains the principal therapeutic challenge for patients with more indolent subtypes, driven by a complex interplay between genetic abnormalities intrinsic to the MDS clone and senescence dependent inflammatory signals within the bone marrow (BM) microenvironment. Although three agents are approved for the treatment of MDS in the United States (US), lenalidomide (LEN) represents the only targeted therapeutic. Treatment with LEN yields sustained red blood cell transfusion independence accompanied by partial or complete resolution of cytogenetic abnormalities in the majority of patients with a chromosome 5q deletion (del5q), whereas only a minority of patients with non-del5q MDS achieve a meaningful response, infrequently accompanied by cytogenetic improvement. Although responses in patients with del5q MDS are relatively durable, lasting a median of 2.5 years, resistance emerges over time with resumption of transfusion dependence.

SUMMARY

Disclosed is a method for treating myeloid disorders, such as meylodysplastic syndrome (MDS), in a subject that involves administering to the subject a therapeutically effective amount of a protein phosphatase 2A (PP2A) inhibitor. In some cases, the subject has del(5q) MDS. In other cases, the subject has non-del(5q) MDS.

In some cases, the method is used to treat a subject that has become resistant to a current therapy, such as lenalidomide, azacitidine, decitabine, dexamethasone, or pharmaceutically acceptable salt thereof. For example, the current therapy can be maintained and supplemented with the composition comprising a PP2A inhibitor, or it can be replaced by PP2A inhibitor treatment.

The PP2A inhibitor can therefore be administered alone or in combination with other treatments. For example, the methods can further involve administering to the subject a therapeutically effective dose of lenalidomide, azacitidine, decitabine, or dexamethasone.

Therefore, also disclosed is a method for treating an MDS in a subject that involves administering to the subject an effective amount of a first composition comprising lenalidomide, or a pharmaceutically acceptable salt thereof; and a second composition comprising a protein phosphatase 2A (PP2A) inhibitor.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
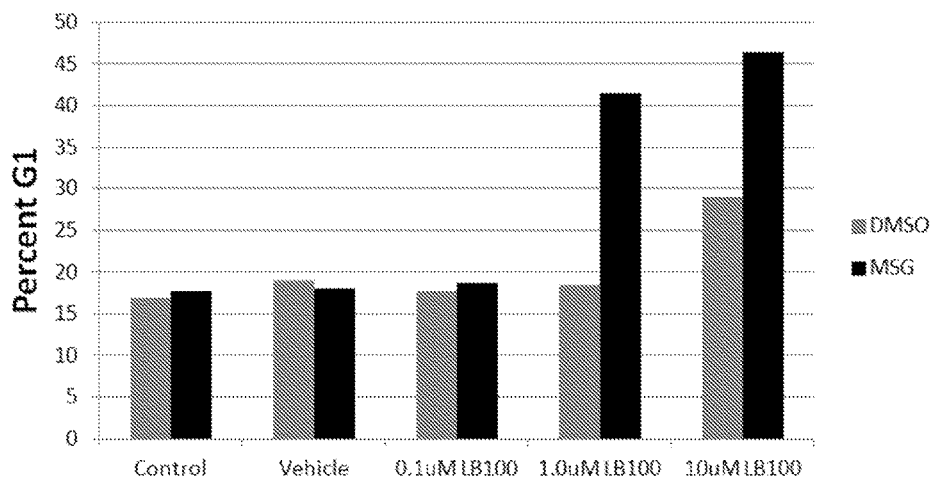
FIG. 1 is a bar graph showing percent of Namalwa cells in G1 arrest 24 hours after treatment with 0.1 µM, 1.0 µM or 10 µM LB-100 dissolved in DMSO (grey) or MSG (black) compared to control and vehicle.

Patients with myelodysplastic syndromes (MDS) have limited treatment options that can offer meaningful long-term response. Many patients in the early stages of the disease receive only supportive care until development of symptomatic cytopenias. Lenalidomide is the drug of choice for lower risk MDS patients with deletion of chromosome 5 (del(5q)), yielding transfusion independence (TI) in 67% of patients compared to 26% in non-del (5q) MDS. Lenalidomide is selectively cytotoxic to del(5q) cells via inhibition of the haplodeficient protein phosphatase 2A (PP2A) and cell division cycle 25C (Cdc25C). PP2A inhibition by lenalidomide stabilizes MDM2 leading to p53 degradation and subsequent arrest of del(5q) progenitors in G2/M, restoring non-clonal erythropoiesis. The magnitude of PP2A reduction at time of response corresponds to duration of response, whereas lenalidomide resistance has been linked to PP2A over-expression and consequent p53 accumulation. In non-del(5q) MDS, lenalidomide enhances erythroid receptor signaling to restore effective erythropoiesis in a subset of patients. PP2A inhibition promotes coalescence of lipid rafts with attendant incorporation and upregulation of the erythropoietin receptor along with its signaling intermediates to yield a more efficient receptor signaling platform. Therefore, PP2A as an attractive therapeutic target in the treatment of myeloid disorders, such as MDS.

Protein Phosphatase 2A (PP2A) Inhibitors

Protein phosphatase 2A (PP2A) is a ubiquitous serine/threonine phosphatase that dephosphorylates numerous proteins of both ATM/ATR-dependent and -independent response pathways. PP2A inhibitors are known in the art and can be identified by screening compound libraries. For example, cantharidin is an active constituent of mylabris, a traditional Chinese medicine, and is a potent and selective inhibitor of PP2A.

Okadaic acid (9,10-Deepithio-9,10-didehydroacanthifolicin) is a potent inhibitor of protein phosphatase 1 ($IC_{50}$=3-15 nM) and protein phosphatase 2A ($IC_{50}$=0.1-1 nM). It is highly selective over PP2B, PP2C and a range of other phosphatases. Although cantharadin has previously been used in the treatment of hepatomas and has shown efficacy against multidrug-resistant leukemia cell lines, its severe toxicity limits its clinical usefulness. LB100 is a small molecule derivative of cantharadin with significantly less toxicity.

In some embodiments, the PP2A inhibitor is LB100, which has the structure:

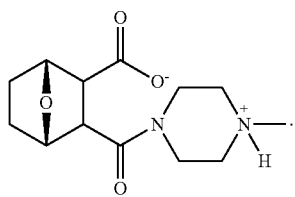

LB-100 has been approved by the Food and Drug Administration for Phase I study in patients with advanced cancers given alone and then in combination with a widely used anticancer drug, docetaxel. Additional, non-limiting examples of PP2A inhibitors related to LB100 are described, for example, in WO 2014/005084 and WO/2010/014254 by Lixte Biotechnology, Inc, which is incorporated by reference herein in its entirety for the teaching of these inhibitors.

A method for treating myelodysplastic syndrome (MDS) in a subject afflicted therewith is disclosed that involves administering to the subject a therapeutically effective amount of a protein phosphatase 2A (PP2A) inhibitor. In some embodiments, the MDS is del(5q) MDS). In some embodiments, the MDS is non-del(5q) MDS. In some embodiments, the MDS is characterized by refractory anemia (RA), refractory neutropenia (RN), and/or refractory thrombocytopenia (RT). In some embodiments, the MDS is characterized by refractory anemia (RA) with ringed sideroblasts (RARS). In some embodiments, the MDS is characterized by refractory cytopenia with multilineage dysplasia (RCMD). In some embodiments, the MDS is characterized by refractory cytopenia with multilineage dysplasia and ringed sideroblasts (RCMD-RS). In some embodiments, MDS is characterized by refractory anemia (RA) with excess blasts-1 (RAEB-1). In some embodiments, the MDS is characterized by refractory anemia (RA) with excess blasts-2 (RAEB-2). In some embodiments, the MDS is characterized by refractory anemia (RA) with excess Blasts in Transformation (RAEB-t). In some embodiments, the MDS is unclassified myelodysplastic syndrome (MDS-U).

In some embodiments of the method, the subject has become resistant to or non-responsive to a current therapy. In some embodiments, the MDS has become resistant to a current therapy. In some embodiments, the current therapy comprises lenalidomide, or a pharmaceutically acceptable salt thereof. In some embodiments, the current therapy comprises azacitidine, decitabine, or a pharmaceutically acceptable salt thereof. In some embodiments, the resistance is caused by an upregulation of protein phosphatase 2A (PP2A) activity.

In some embodiments, the current therapy is maintained and supplemented with a composition comprising a protein phosphatase 2A (PP2A) inhibitor. In some embodiments, the method further comprising administering to the subject a therapeutically effective amount of lenalidomide (LEN). In some embodiments, the subject was previously treated with lenalidomide. In some embodiments, the MDS in the subject is resistant to lenalidomide. In some embodiments, the PP2A inhibitor reduces or reverses the resistance of the MDS to the lenalidomide. In some embodiments, the compound re-sensitizes the MDS to the lenalidomide. In some embodiments, the method further comprising administering to the subject a therapeutically effective amount of dexamethasone.

Also disclosed is a method for treating a myelodysplastic syndrome (MDS) in a subject that involves administering to the subject an effective amount of a first composition comprising lenalidomide, or a pharmaceutically acceptable salt thereof; and a second composition comprising a protein phosphatase 2A (PP2A) inhibitor. In some embodiments, the treating comprises reducing the number of blasts in the bone marrow or peripheral blood of the subject. In some embodiments, the treating comprises reducing the number of myeloblasts in the bone marrow or peripheral blood of the subject. In some embodiments, the treating comprises reducing the number of sideroblasts or ringed sideroblasts in the bone marrow or peripheral blood of the subject. In some embodiments, the treating comprises increasing the concentration of normal red blood cells, normal white blood cells and/or platelets in the subject. In some embodiments, the treating comprises increasing the concentration of hemoglobin in the subject. In some embodiments, the PP2A inhibitor inhibits PP2A activity in hematopoietic stem cells and/or progenitor cells in the subject. In some embodiments, the MDS in the subject is low risk MDS based on the IPSS system. In some embodiments, the MDS in the subject is intermediate-1 risk MDS based on the IPSS system. In some embodiments, the MDS in the subject is intermediate-2 risk MDS based on the IPSS system. In some embodiments, the MDS in the subject is high risk MDS based on the IPSS system.

In some embodiments, the PP2A inhibitor is a compound having the structure:

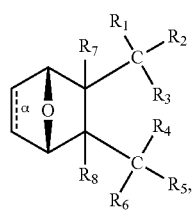

wherein:
bond α is present or absent;
$R_1$ and $R_2$ together are =O;
$R_3$ is OH, O⁻, OR$_9$, O(CH$_2$)$_{1-6}$R$_9$, SH, S⁻, or SR$_9$,
  wherein $R_9$ is H, alkyl, alkenyl, alkynyl or aryl;

$R_4$ is

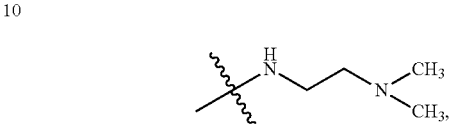

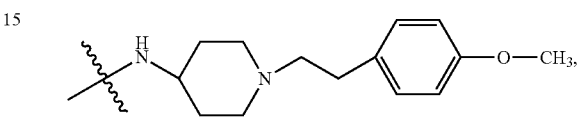

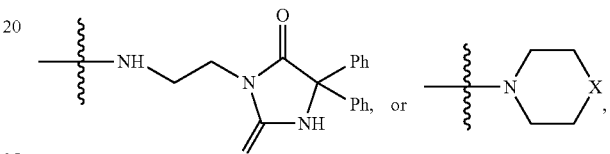

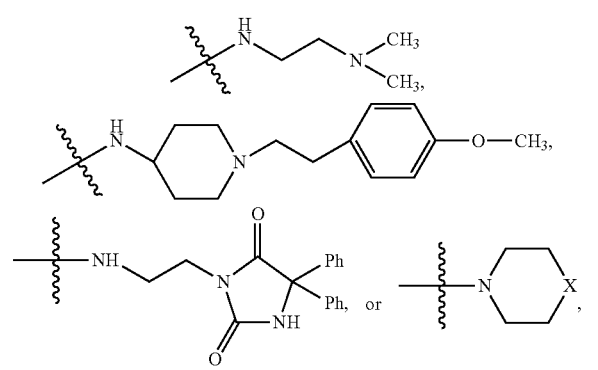

—CH$_2$CN, —CH$_2$CO$_2$R$_{11}$, or —CH$_2$COR$_{11}$,
  wherein each $R_{11}$ is independently H, alkyl, alkenyl or alkynyl;
$R_5$ and $R_6$ taken together are =O;
$R_7$ and $R_8$ are each H,
or a salt, zwitterion, or ester thereof, so as to thereby treat the myelodysplastic syndrome in the subject.

In some embodiments, the PP2A inhibitor has the structure:

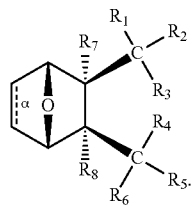

In some embodiments, bond α in the compound is present. In some embodiments, bond α in the compound is absent.

In some embodiments,
$R_3$ is OH, O⁻, or OR$_9$,
  wherein $R_9$ is alkyl, alkenyl, alkynyl or aryl;
$R_4$ is

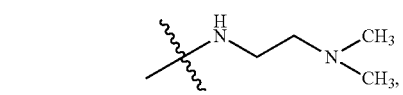

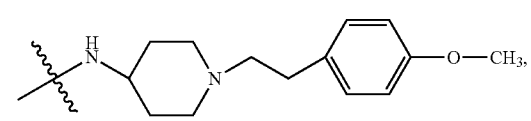

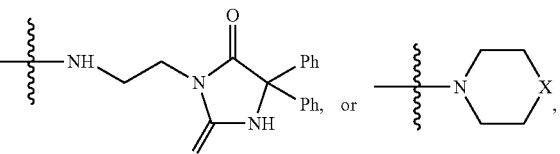

where X is O, S, NR$_{10}$, N⁺$^{HR}$$_{10}$ or N⁺R$_{10}$R$_{10}$,
  where each $R_{10}$ is independently H, alkyl, alkenyl, alkynyl, aryl,

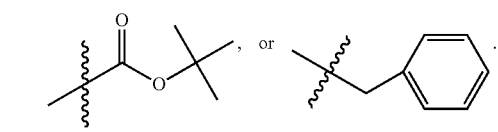

In some embodiments,
$R_3$ is OH, O⁻ or OR$_9$,
  where $R_9$ is H, methyl, ethyl or phenyl.
In some embodiments,
$R_3$ is OH, O⁻ or OR$_9$,
  wherein $R_9$ is methyl.
In some embodiments,
$R_4$ is

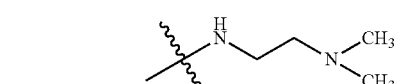

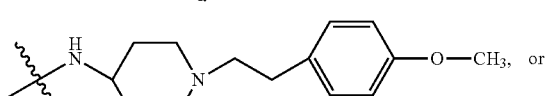

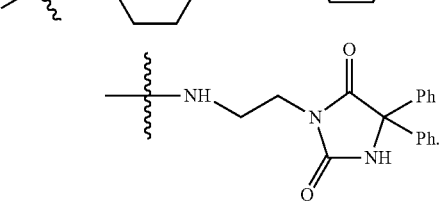

In some embodiments, $R_4$ is

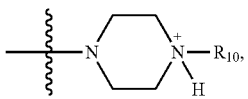

wherein $R_{10}$ is H, alkyl, alkenyl, alkynyl, aryl, or

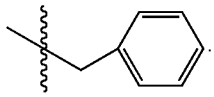

In some embodiments, $R_4$ is

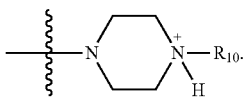

wherein $R_{10}$ is —H, —CH$_3$, —CH$_2$CH$_3$, or

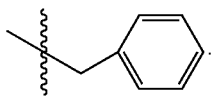

In some embodiments, $R_4$ is

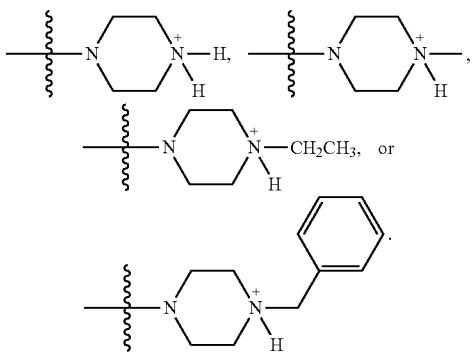

In some embodiments, $R_4$ is

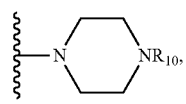

wherein $R_{10}$ is H, alkyl, alkenyl, alkynyl, aryl,

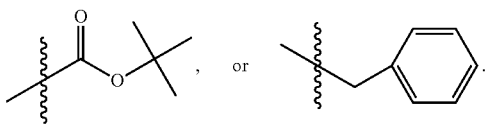

In some embodiments, $R_4$ is

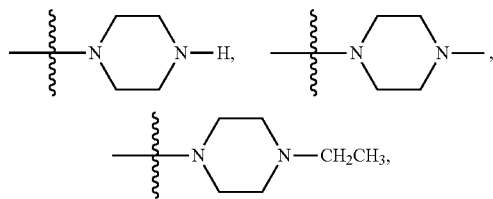

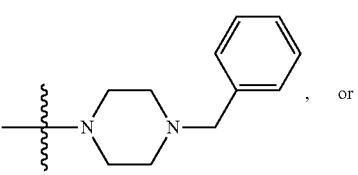

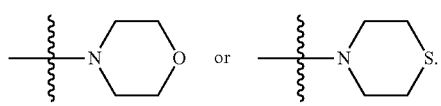

In some embodiments, $R_4$ is

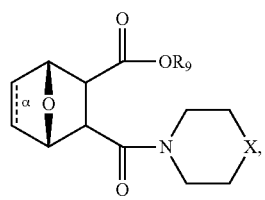

In some embodiments, the PP2A inhibitor has the structure

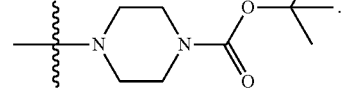

wherein bond α is present or absent;

$R_9$ is present or absent and when present is H, alkyl, alkenyl, alkynyl or phenyl; and X is O, NR$_{10}$, NH$^+$R$_{10}$ or N$^+$R$_{10}$R$_{10}$, where each $R_{10}$ is independently H, alkyl, substituted alkyl, alkenyl, substituted alkenyl, alkynyl, substituted alkynyl, aryl,

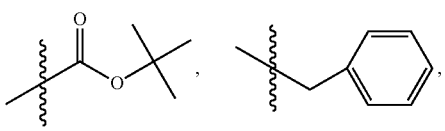

—CH$_2$CN, —CH$_2$CO$_2$R$_{12}$, or —CH$_2$COR$_{12}$, where $R_{12}$ is H or alkyl, or a salt, zwitterion or ester thereof.

In some embodiments, the PP2A inhibitor has the structure

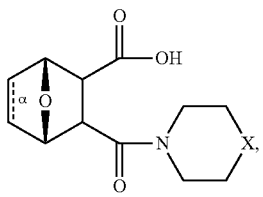

wherein
bond α is present or absent;
X is O or $NR_{10}$,
 where each $R_{10}$ is independently H, alkyl, substituted alkyl, alkenyl, substituted alkenyl, alkynyl, substituted alkynyl, aryl,

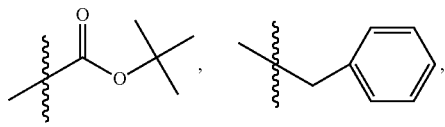

—$CH_2CN$, —$CH_2CO_2R_{12}$, or —$CH_2COR_{12}$,
 where $R_{12}$ is H or alkyl,
or a salt, zwitterion or ester thereof.

In some embodiments, the PP2A inhibitor has the structure

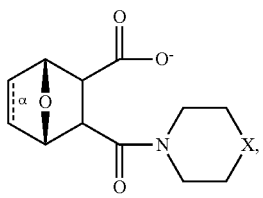

wherein
bond α is present or absent;
X is O or $NH^+R_{10}$,
 where $R_{10}$ is H, alkyl, substituted alkyl, alkenyl, substituted alkenyl, alkynyl, substituted alkynyl, aryl,

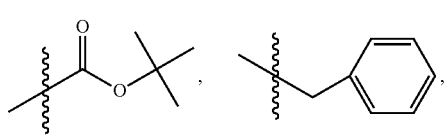

—$CH_2CN$, —$CH_2CO_2R_{12}$, or —$CH_2COR_{12}$,
 where $R_{12}$ is H or alkyl,
or a salt, zwitterion or ester thereof.

In some embodiments, the PP2A inhibitor has the structure

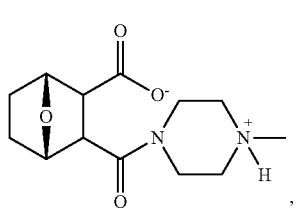

or a salt or ester thereof.

In some embodiments, the PP2A inhibitor has the structure

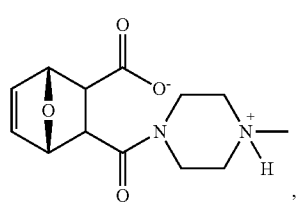

or a salt or ester thereof.

Also, in some embodiments, the protein phosphatase 2A (PP2A) inhibitor has the structure:

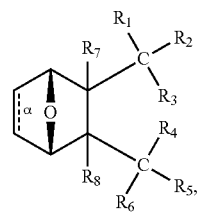

wherein
bond α is present or absent;
$R_1$ and $R_2$ is each independently H, O⁻ or $OR_9$,
 where $R_9$ is H, alkyl, alkenyl, alkynyl or aryl,
 or $R_1$ and $R_2$ together are =O;
$R_3$ and $R_4$ are each different, and each is OH, O⁻, $OR_9$, $OR_{10}$,
$O(CH_2)_{1-6}R_9$, SH, S⁻, $SR_9$,

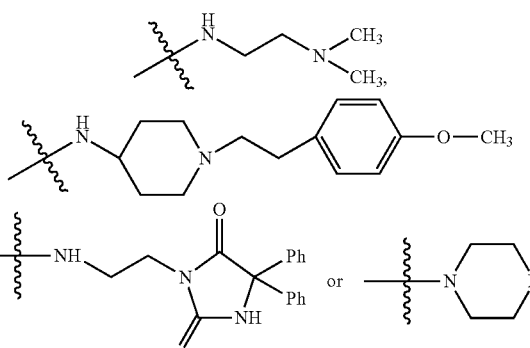

where X is O, S, $NR_{10}$, or $N+R_{10}R_{10}$,
 where each $R_{10}$ is independently H, alkyl, $C_2$-$C_{12}$ alkyl, alkenyl, $C_4$-$C_{12}$ alkenyl, alkynyl, aryl, substituted aryl where the substituent is other than chloro when Ri and $R_3$ are =O,

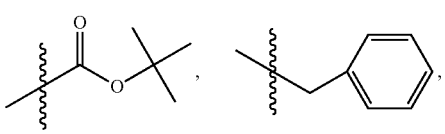

—$CH_2CN$, —$CH_2CO_2R_{11}$, —$CH_2COR_{11}$, —$NHR_{11}$ or —$NH^*(R_{11})_2$,
 wherein each $R_{11}$ is independently alkyl, alkenyl or alkynyl, or H;

$R_5$ and $R_6$ is each independently H, OH, or $R_5$ and $R_6$ taken together are =O;
$R_7$ and $R_8$ is each independently H, F, Cl, Br, $SO_2Ph$, $CO_2CH_3$, or $SR_{12}$,
where $R_{12}$ is H, alkyl, alkenyl, alkynyl or aryl; and
each occurrence of alkyl, alkenyl, or alkynyl is branched or unbranched, unsubstituted or substituted,
or a salt, enantiomer, zwitterion, or ester of the compound.

In one embodiment, the protein phosphatase 2A inhibitor has the structure

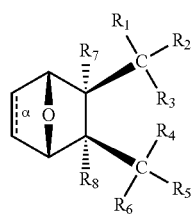

In one embodiment, the protein phosphatase 2A inhibitor has the structure

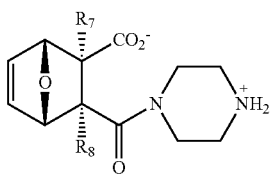

In one embodiment, the protein phosphatase 2A inhibitor has the structure

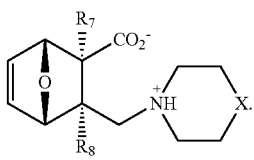

In one embodiment, bond α is present. In another embodiment, bond α is absent. In one embodiment, $R_1$ and $R_2$ together are =O;
$R_3$ is O⁻ or $OR_9$, where $R_9$ is H, methyl, ethyl or phenyl;
$R_4$ is

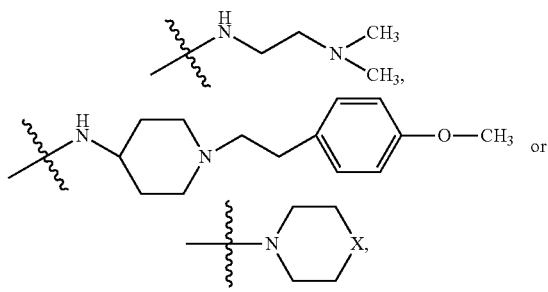

where X is O, S, $NR_{10}$, or $N^+R_{10}R_{10}$,
where each $R_{10}$ is independently H, alkyl, substituted $C_2$-$C_{12}$ alkyl, alkenyl, substituted $C_4$-$C_{12}$ alkenyl, alkynyl substituted alkynyl, aryl, substituted aryl where the substituent is other than chloro,

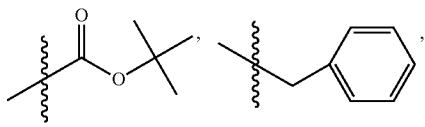

—$CH_2CN$, —$CH_2CO_2R_{11}$, —$CH_2COR_{11}$, —$NR_{11}$ or —$NH^+(R_{11})_2$,
where $R_{11}$ is alkyl, alkenyl or alkynyl, each of which is substituted or unsubstituted, or H;

$R_5$ and $R_6$ taken together are =O; and $R_7$ and $R_8$ is each independently H, F, Cl, Br, $SO_2Ph$, $CO_2CH_3$, or $SR_{12}$, where $R_{12}$ is a substituted or unsubstituted alkyl, alkenyl alkynyl.

In one embodiment, $R_4$ is O⁻.

In another embodiment, $R_4$ is

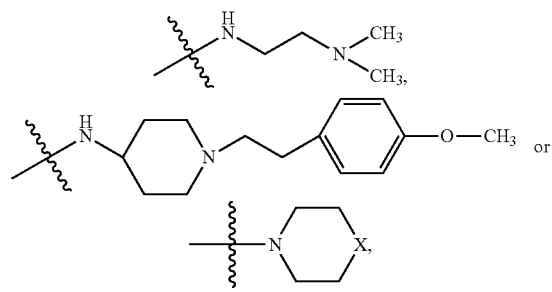

where X is O, S, $NR_{10}$, or $N^+R_{10}R_{10}$
where each $R_{10}$ is independently H, alkyl, substituted $C_2$-$C_{12}$ alkyl, alkenyl, substituted $C_4$-$C_{12}$ alkenyl, alkynyl, substituted alkynyl, aryl, substituted aryl where the substituent is other than chloro when $R_1$, and $R_2$ are =O,

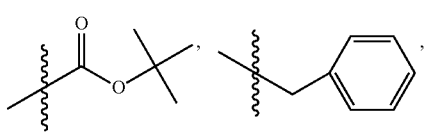

—$CH_2CN$, —$CH_2CO_2R_{11}$, —$CH_2COR_{11}$, —$NHR_{11}$ or —$NH^+(R_{11})_2$,
where $R_{11}$ is H or alkyl.

In one embodiment, the protein phosphatase inhibitor 2A has the structure

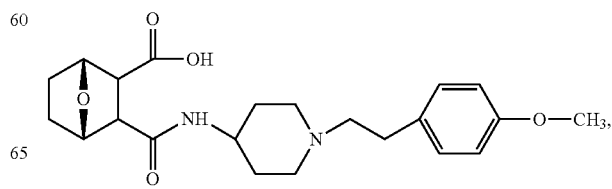

-continued

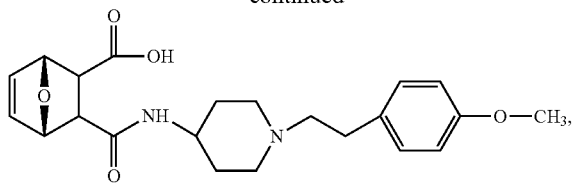

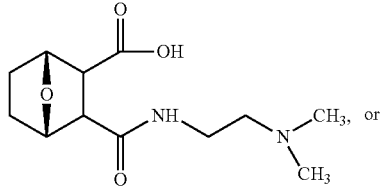

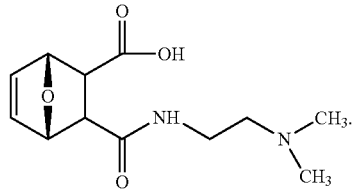

In one embodiment, $R_4$ is

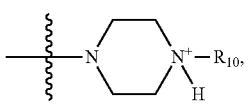

where $R_{10}$ is H, alkyl, substituted $C_2$-$C_{12}$ alkyl, alkenyl, substituted $C_4$-$C_{12}$ alkenyl, alkynyl, substituted alkynyl, aryl, substituted aryl where the substituent is other than chloro when $R_1$ and $R_2$ are =O,

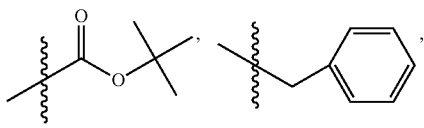

—$CH_2CN$, —$CH_2CO_2R_{11}$, —$CH_2COR_{11}$, —$NHR_{11}$ or —$NH^+(R_{11})_2$, where $R_{11}$ is H or alkyl.

In one embodiment, $R_4$ is

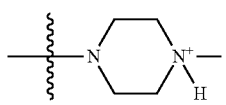 [SMILES: *N1CC[NH+](C)CC1]

In one embodiment, $R_4$ is

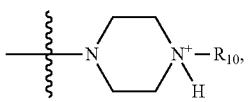

where $R_{10}$ is

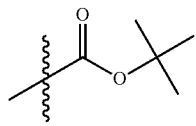 [SMILES: *C(=O)OC(C)(C)C]

In one embodiment, $R_4$ is

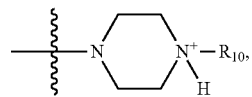

where $R_{10}$ is

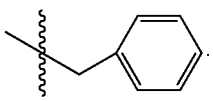

In one embodiment, $R_4$ is

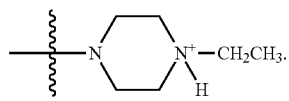

In one embodiment, $R_4$ is

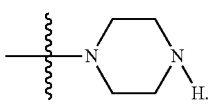

In one embodiment, $R_5$ and $R_6$ together are =O. In another embodiment, $R_7$ and $R_8$ are each H.

In one embodiment, the protein phosphatase inhibitor 2A has the structure

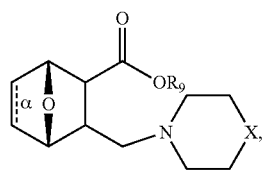

wherein bond α is present or absent;
$R_9$ is present or absent and when present is H, $C_1$-$C_{10}$ alkyl, $C_2$-$C_{10}$ alkenyl or phenyl; and
X is O, S, $NR_{10}$ or $N^+R_{10}R_{10}$,
where each $R_{10}$ is independently H, alkyl, substituted $C_2$-$C_{12}$ alkyl, alkenyl, substituted $C_4$-$C_{12}$ alkenyl, alkynyl, substituted alkynyl, aryl, substituted aryl where the substituent is other than chloro,

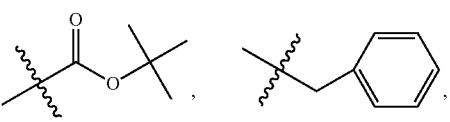

—$CH_2CO_2R_{11}$, —$CH_2COR_{11}$, —$CH_2CN$, or —$CH_2CH_2R_{16}$, where $R_{11}$ is H or alkyl, and where $R_{16}$ is any substituent that is a precursor to an aziridinyl intermediate,
or a salt, zwitterion, enantiomer, or ester of the compound.

In one embodiment, the protein phosphatase 2A inhibitor has the structure

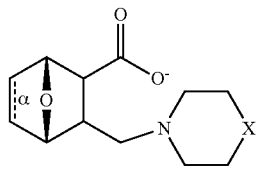

wherein bond α is present or absent;
X is O, S, $NR_{10}$ or $N^+R_{10}R_{10}$,
where each $R_{10}$ is independently H, alkyl, substituted $C_2$-$C_{12}$ alkyl, alkenyl, substituted $C_4$-$C_{12}$ alkenyl, alkynyl, substituted alkynyl, aryl, substituted aryl where the substituent is other than chloro,

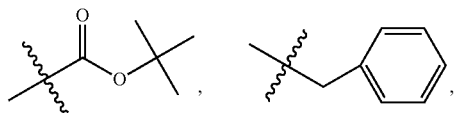

—$CH_2CO_2R_{11}$, —$CH_2COR_{11}$, —$CH_2CN$, or —$CH_2CH_2R_{16}$, where $R_{11}$ is H or alkyl, and where Rib is any substitutent that is a aziridinyl intermediate,
or a salt, zwitterion, enantiomer, or ester of the compound.
In one embodiment, X is O or $NH^+R_{10}$,
where $R_{10}$ is H, alkyl, substituted $C_2$-$C_{12}$ alkyl, alkenyl, substituted $C_4$-$C_{12}$ alkenyl, alkynyl, substituted alkynyl, aryl, substituted aryl where the substituent is other than chloro,

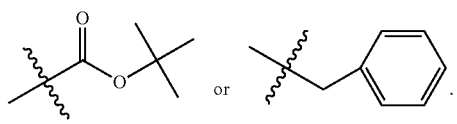

In one embodiment, X is —$CH_2CH_2R_{16}$,
where $R_{16}$ is any substitutent that is a precursor to an aziridinyl intermediate.
In one embodiment, X is O.
In another embodiment, X is $NH^+R_{10}$,
where $R_{10}$H, alkyl, substituted $C_2$-$C_{12}$ alkyl, alkenyl, substituted $C_4$-$C_{12}$ alkenyl, alkynyl, substituted alkynyl, aryl, substituted aryl where the substituent is other than chloro,

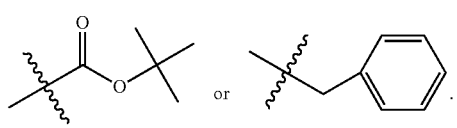

In one embodiment, $R_{10}$ is methyl. In another embodiment $R_{10}$ is

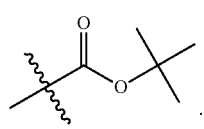 [SMILES: *C(=O)OC(C)(C)C]

In one embodiment, $R_{10}$ is

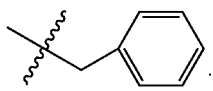

In one embodiment, $R_{10}$ is ethyl. In another embodiment, $R_{10}$ is absent.
In one embodiment, the protein phosphatase 2A inhibitor has the structure

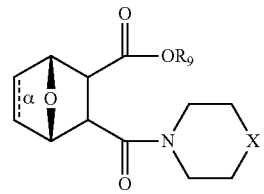

wherein bond α is present or absent;
$R_9$ is present or absent and when present is H, alkyl, alkenyl, alkynyl or phenyl; and
X is O, $NR_{10}$, or $N^+R_{10}R_{10}$,
where each $R_{10}$ is independently H, alkyl, substituted $C_2$-$C_{12}$ alkyl, alkenyl, substituted $C_4$-$C_{12}$ alkenyl, alkynyl, substituted alkynyl, aryl, substituted aryl where the substituent is other than chloro,

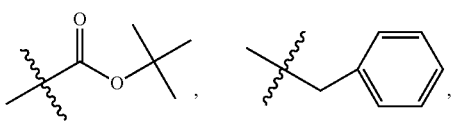

—$CH_2CN$, —$CH_2CO_2R_{12}$, or —$CH_2COR_{12}$,
where $R_{12}$ is H or alkyl,
or a salt, zwitterion, enantiomer, or ester of the compound.
In one embodiment, the protein phosphatase 2A inhibitor has the structure

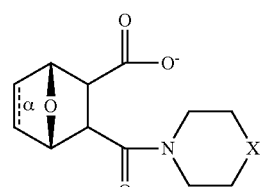

wherein bond α is present or absent;
X is O or $N^+R_{10}$,
where $R_{10}$ is H, alkyl, substituted $C_2$-$C_{12}$ alkyl, alkenyl, substituted $C_4$-$C_{12}$ alkenyl, alkynyl, substituted alkynyl, aryl, substituted aryl where the substituent is other than chloro,

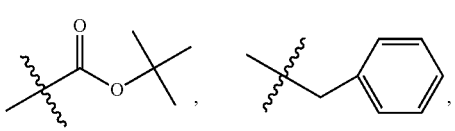

—$CH_2CN$, —$CH_2CO_2R_{12}$, or —$CH_2COR_{12}$, where $R_{12}$ is H or alkyl.

In one embodiment, bond α is present. In another embodiment, bond α is absent.

In one embodiment, the protein phosphatase 2A inhibitor has the structure

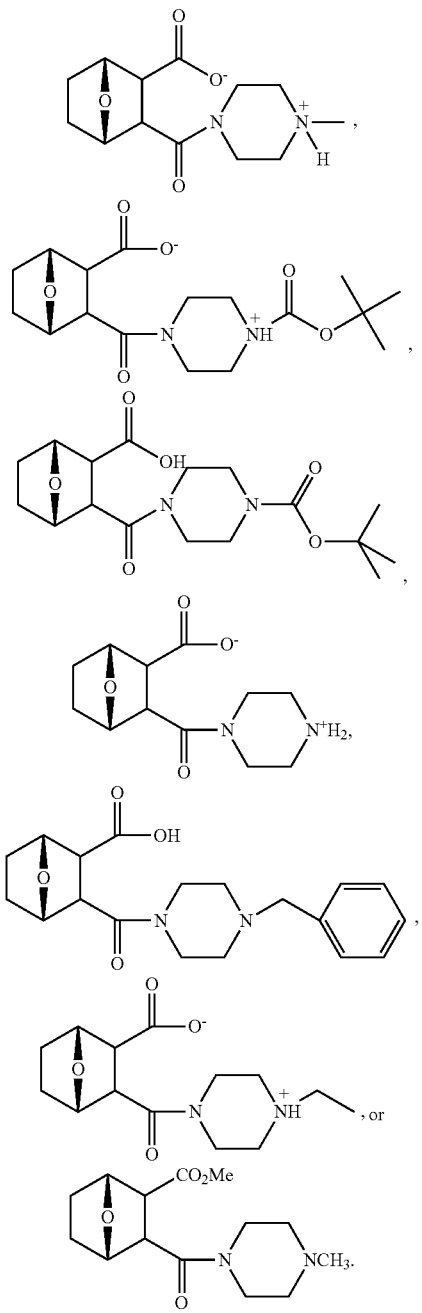

In one embodiment, the protein phosphatase 2A inhibitor has the structure

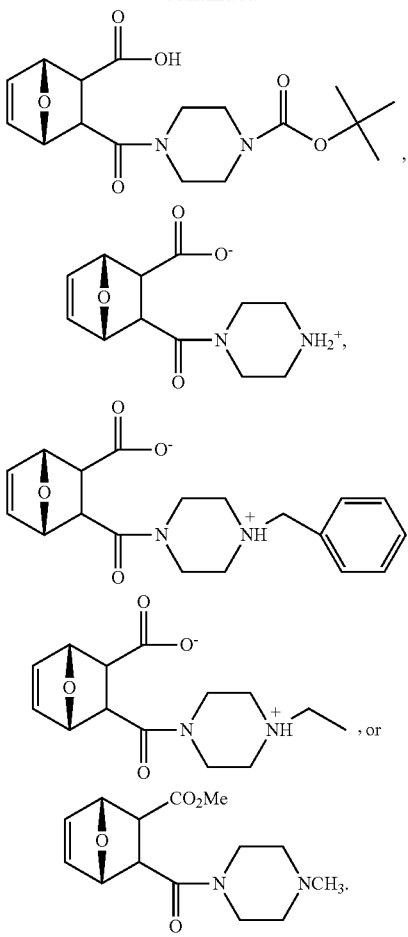

In one embodiment, the protein phosphatase 2A inhibitor has the structure

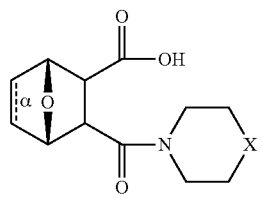

wherein bond α is present or absent;

X is $NH^+R_{10}$, where $R_{10}$ is present or absent and when present $R_{10}$ is alkyl, substituted $C_2$-$C_{12}$ alkyl, alkenyl, substituted $C_4$-$C_{12}$ alkenyl,

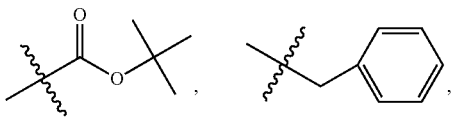

—$CH_2CN$, —$CH_2CO_2R_{12}$, or —$CH_2COR_{12}$ where $R_{12}$ is H or alkyl.

In one embodiment of the method, the protein phosphatase inhibitor has the structure

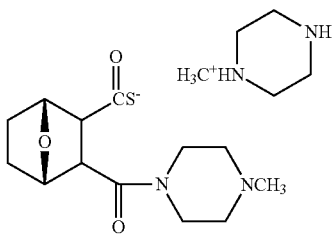

In one embodiment of the method, the protein phosphatase inhibitor has the structure

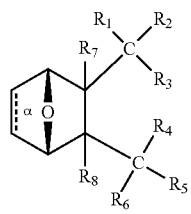

wherein bond α is present or absent;
$R_1$ and $R_2$ is each independently H, O⁻ or $OR_9$,
  where $R_9$ is H, alkyl, substituted alkyl, alkenyl, alkynyl or aryl,
or $R_1$ and $R_2$ together are =O;
$R_3$ and $R_4$ are each different, and each is $O(CH_2)_{1-6}R_9$ or $OR_9$,
or

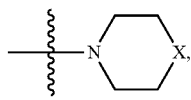

where X is O, S, $NR_{10}$, or $N^+R_{10}R_{10}$,
  where each $R_{10}$ is independently H, alkyl, hydroxyalkyl, $C_2$-$C_{12}$ alkyl, alkenyl, $C_4$-$C_{12}$ alkenyl, alkynyl, aryl, substituted aryl where the substituent is other than chloro when $R_1$ and $R_2$ are =O,

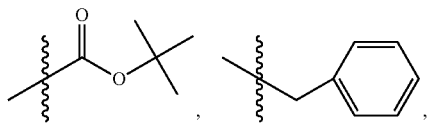

—$CH_2CN$, —$CH_2CO_2R_{11}$, —$CH_2COR_{11}$, —$NHR_{11}$ or —$NH^+(R_{11})_2$,
  where each $R_{11}$ is independently alkyl, alkenyl or alkynyl, each of
  which is substituted or unsubstituted, or H
or $R_3$ and $R_4$ are each different and each is OH or

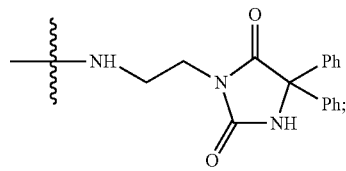 [SMILES: *NCCN1C(=O)NC(c2ccccc2)(c2ccccc2)C1=O]

$R_5$ and $R_6$ is each independently H, OH, or $R_5$ and $R_6$ taken together are =O;

$R_7$ and $R_8$ is each independently H, F, Cl, Br, $SO_2Ph$, $CO_2CH_3$, $SR_{12}$,
  where $R_{12}$ is H, aryl or a substituted or unsubstituted alkyl, alkenyl or alkynyl; and
each occurrence of alkyl, alkenyl, or alkynyl is branched or unbranched, unsubstituted or substituted,
or a salt, zwitterion, enantiomer, or ester of the compound.

In one embodiment, the protein phosphatase 2A inhibitor has the structure

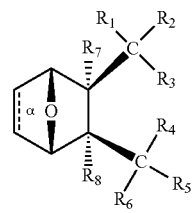

In one embodiment of the method, the bond α is present.
In one embodiment of the method, the bond is absent.
In one embodiment of the method,
$R_3$ is $O(CH_2)_{1-6}R_9$ or $OR_{10}$,
  where $R_9$ is aryl, substituted ethyl or substituted phenyl, wherein the substituent is in the para position of the phenyl;
$R_4$ is

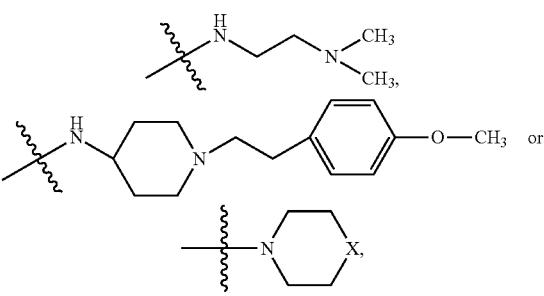

where X is O, S, $NR_{10}$, or $N^+R_{10}R_{10}$,
where each $R_{10}$ is independently H, alkyl, hydroxyalkyl, substituted $C_2$-$C_{12}$ alkyl, alkenyl, substituted $C_4$-$C_{12}$ alkenyl, alkynyl, substituted alkynyl, aryl, substituted aryl where the substituent is other than chloro,

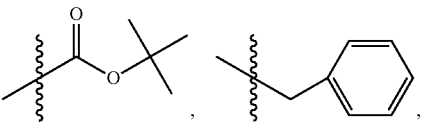

—$CH_2CN$, —$CH_2CO_2R_{11}$, —$CH_2COR_{11}$, —$NHR_{11}$ or —$NH^+(R_{11})_2$,
  where $R_{11}$ is alkyl, alkenyl or alkynyl, each of which is substituted or unsubstituted, or H;
or where $R_3$ is OH and $R_4$ is

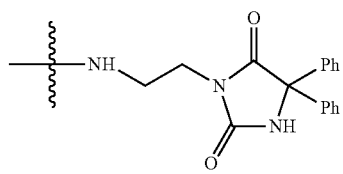 [SMILES: *NCCN1C(=O)NC(c2ccccc2)(c2ccccc2)C1=O]

In one embodiment of the method, $R_4$ is

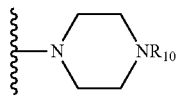

where $R_{10}$ is alkyl or hydroxylalkyl
or $R_4$ is

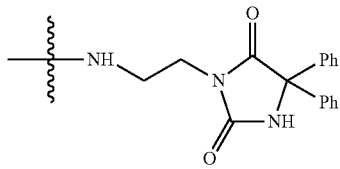

where $R_3$ is OH.

In one embodiment,
$R_1$ and $R_2$ together are =O;
$R_3$ is $O(CH_2)_{1-2}R_9$ or $OR_{10}$,
where $R_9$ is aryl, substituted ethyl, or substituted phenyl, wherein the substituent
is in the para position of the phenyl;
or $R_3$ is OH and $R_4$ is

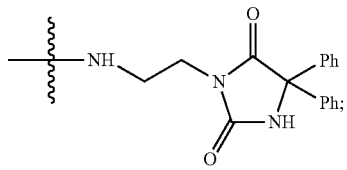 [SMILES: *NCCN1C(=O)NC(c2ccccc2)(c2ccccc2)C1=O]

$R_4$ is

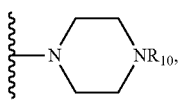

where $R_{10}$ is alkyl or hydroxyl alkyl;
$R_5$ and $R_6$ together are =O; and
$R_7$ and $R_8$ are each independently H.

In one embodiment,
$R_1$ and $R_2$ together are =O;
$R_3$ is OH, $O(CH_2)R_9$, or $OR_9$,
where $R_9$ is phenyl or $CH_2CCl_3$,

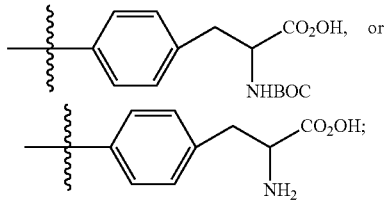

$R_4$ is

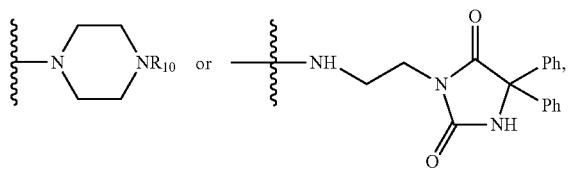

where $R_{10}$ is $CH_3$ or $CH_3CH_2OH$;
$R_5$ and $R_6$ together are =O; and
$R_7$ and $R_8$ are each independently H.

In one embodiment,
$R_3$ is $OR_9$
where $R_9$, is $(CH_2)_{1-6}(CHNHBOC)CO_2H$, $(CH_2)_{1-6}(CHNH_2)CO_2H$, or $(CH_2)_{1-6}CCl_3$.

In one embodiment,
$R_9$ is $CH_2(CHNHBOC)CO_2H$, $CH_2(CHNH_2)CO_2H$, or $CH_2CCl_3$.

In one embodiment,
$R_3$ is $O(CH_2)_{1-6}R_9$ or $O(CH_2)R_9$,
where $R_9$ is phenyl.

In one embodiment,
$R_3$ is $O(CH_2)R_9$,
where $R_9$ is phenyl.

In one embodiment,
$R_3$ is OH and $R_4$ is

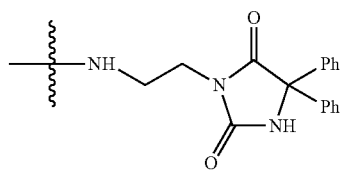 [SMILES: *NCCN1C(=O)NC(c2ccccc2)(c2ccccc2)C1=O]

In one embodiment,
$R_4$ is

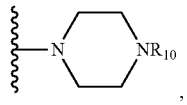

wherein $R_{10}$ is alkyl or hydroxyalkyl.
In one embodiment, $R_{10}$ is $-CH_2CH_2OH$ or $-CH_3$.
In one embodiment, the protein phosphatase inhibitor has the structure

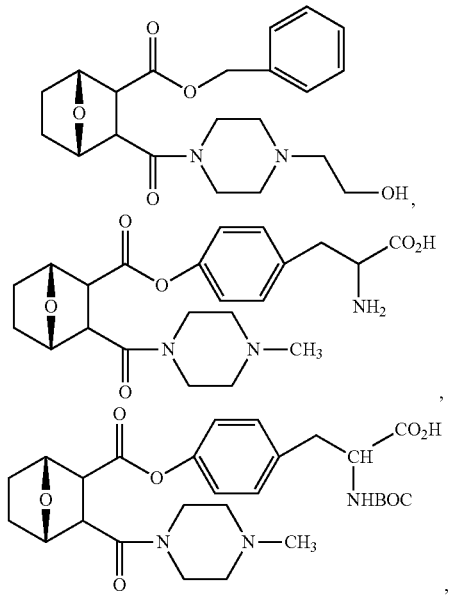

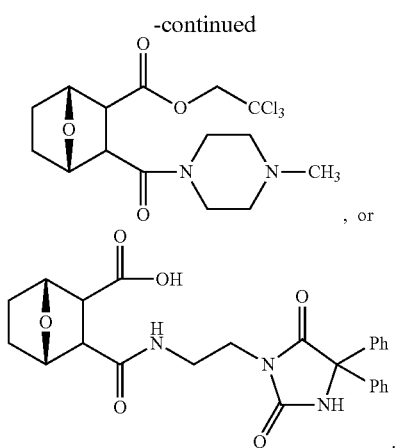

In one embodiment of the method, the protein phosphatase inhibitor has the structure

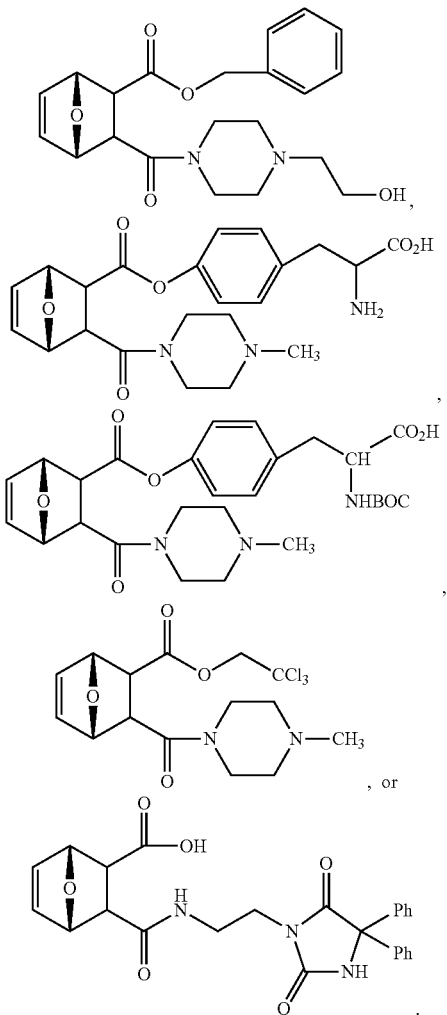

In some embodiments of the method, the amount of the PP2A inhibitor and the amount of the lenalidomide are each periodically administered to the subject. In some embodiments of the method, the amount of the compound and the amount of the lenalidomide are administered simultaneously, separately or sequentially. In some embodiments of the method, the amount of the compound and the amount of the lenalidomide when taken together is more effective to treat the subject than when the compound or the lenalidomide is administered alone. In some embodiments of the method, the amount of the compound and the amount of the lenalidomide when taken together has a greater than additive effect on the MDS in the subject. In some embodiments of the method, the amount of the compound and the amount of the myelodysplastic syndrome when taken together is effective to reduce a clinical symptom of the MDS in the subject.

Also disclosed is a pharmaceutical composition comprising a PP2A inhibitor and at least one pharmaceutically acceptable carrier for use in treating MDS. Also disclosed is a pharmaceutical composition comprising a PP2A inhibitor and lenalidomide, and at least one pharmaceutically acceptable carrier for use in treating MDS. In some embodiments, the pharmaceutically acceptable carrier comprises a liposome. In some embodiments of the pharmaceutical composition, the PP2A inhibitor is contained in a liposome or microsphere, or the compound and the lenalidomide are contained in a liposome or microsphere. Also disclosed is a pharmaceutical composition comprising an amount a PP2A inhibitor for use in treating a subject afflicted with MDS as an add-on therapy or in combination with, or simultaneously, contemporaneously or concomitantly with lenalidomide.

In some embodiments of any of the above methods or uses, the compound and/or the lenalidomide is orally administered to the subject. In some embodiments, the subject is transfusion dependent prior to treatment. some embodiments, the subject is transfusion independent following treatment.

In some embodiments of any of the above methods, the MDS is primary (where no apparent risk factors are found) or secondary (where the MDS develops after being exposed to, for example, chemotherapy or radiation therapy, or exposure to industrial chemicals such as benzene).

The first International Prognostic Scoring System (IPSS) was derived from a study published in 1997 and separates patients into four categories: low risk, intermediate-1 risk, intermediate-2 risk, and high risk (Greenberg P, Cox C, LeBeau M M, et al. International scoring system for evaluating prognosis in myelodysplastic syndromes. Blood 1997; 89:2079-2088). A revised IPSS was developed in 2012 and separates patients into five categories: very low risk, low risk, intermediate risk, high risk, and very high risk (Greenberg P L, Tuechler H, Schanz J, et al. Revised international prognostic scoring system for myelodysplastic syndromes. Blood 2012; 120:2454-2465).

For the foregoing embodiments, each embodiment disclosed herein is contemplated as being applicable to each of the other disclosed embodiments. Thus, all combinations of the various elements described herein are within the scope of the invention.

Pharmaceutical Composition

Also disclosed is a pharmaceutical composition comprising the disclosed molecule in a pharmaceutically acceptable carrier. Pharmaceutical carriers are known to those skilled in the art. These most typically would be standard carriers for administration of drugs to humans, including solutions such as sterile water, saline, and buffered solutions at physiological pH. For example, suitable carriers and their formulations are described in Remington: The Science and Practice of Pharmacy (21 ed.) ed. P P. Gerbino, Lippincott Williams & Wilkins, Philadelphia, Pa. 2005. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. The solution should be RNAse free. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of composition being administered.

Pharmaceutical compositions may include carriers, thickeners, diluents, buffers, preservatives, surface active agents and the like in addition to the molecule of choice. Pharmaceutical compositions may also include one or more active ingredients such as antimicrobial agents, antiinflammatory agents, anesthetics, and the like.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

Methods of Treatment

The compounds used in the disclosed method are protein phosphatase 2A (PP2A) inhibitors. Methods of preparation may be found in U.S. Pat. No. 7,998,957 B2 and U.S. Pat. No. 8,426,444 B2. Compound LB-100 is an inhibitor of PP2A in vitro in human cancer cells and in xenografts of human tumor cells in mice when given parenterally in mice.

Lenalidomide is an effective treatment for MDS patients with chromosome 5q deletion. Without wishing to be bound by any scientific theory, the activity of lenalidomide is attributed at least in part to its phosphatase activity. LB100, a more potent inhibitor, is effective in treating MDS.

Without wishing to be bound by any scientific theory, resistance of MDS to lenalidomide is due at least in part to an increase in PP2A activity. Treatment of a subject afflicted lenalidomide resistant MDS with LB100 re-sensitizes the MDS to the lenalidomide.

Elaboration of LB100 at the $R_1$-$R_8$ positions results in analogs that have similar PP2A inhibitory activity. Thus, each of the disclosed LB100 analogs has analogous activity to LB-100 and behaves similarly in the in vitro and in vivo assays. Accordingly, the LB100 analogs disclose herein, alone or in combination with other agents, are useful in treating MDS.

Disclosed is a method for treating myeloid disorders in a subject by administering to the subject a therapeutically effective amount of the disclosed pharmaceutical composition. The method can further involve administering to the subject lenalidomide, or an analogue or derivative thereof.

In some cases, the myeloid disorder is a myelodysplastic syndrome (MDS). MDSs are hematological (blood-related) medical conditions with ineffective production (or dysplasia) of the myeloid class of blood cells. In some cases, the MDS patient has a chromosome 5q deletion (del(5q)). However, in other cases, the patient has non-del5q MDS.

In some cases, the myeloid disorder is a myelodysplastic/ myeloproliferative neoplasms (MDS/MPN). In some cases, the myeloid disorder is a myelodysplastic syndrome with myeloproliferative features. In some cases, the myeloid disorder is a therapy-related myeloid neoplasm.

The disclosed compositions, including pharmaceutical composition, may be administered in a number of ways depending on whether local or systemic treatment is desired, and on the area to be treated. For example, the disclosed compositions can be administered intravenously, intraperitoneally, intramuscularly, subcutaneously, intracavity, or transdermally. The compositions may be administered orally, parenterally (e.g., intravenously), by intramuscular injection, by intraperitoneal injection, transdermally, extracorporeally, ophthalmically, vaginally, rectally, intranasally, topically or the like, including topical intranasal administration or administration by inhalant.

Parenteral administration of the composition, if used, is generally characterized by injection. Injectables can be prepared in conventional forms, either as liquid solutions or suspensions, solid forms suitable for solution of suspension in liquid prior to injection, or as emulsions. A revised approach for parenteral administration involves use of a slow release or sustained release system such that a constant dosage is maintained.

The compositions disclosed herein may be administered prophylactically to patients or subjects who are at risk for MDS. Thus, the method can further comprise identifying a subject at risk for MDS prior to administration of the herein disclosed compostions.

The exact amount of the compositions required will vary from subject to subject, depending on the species, age, weight and general condition of the subject, the severity of the allergic disorder being treated, the particular nucleic acid or vector used, its mode of administration and the like. Thus, it is not possible to specify an exact amount for every composition. However, an appropriate amount can be determined by one of ordinary skill in the art using only routine experimentation given the teachings herein. For example, effective dosages and schedules for administering the compositions may be determined empirically, and making such determinations is within the skill in the art. The dosage ranges for the administration of the compositions are those large enough to produce the desired effect in which the symptoms disorder are affected. The dosage should not be so large as to cause adverse side effects, such as unwanted cross-reactions, anaphylactic reactions, and the like. Generally, the dosage will vary with the age, condition, sex and extent of the disease in the patient, route of administration, or whether other drugs are included in the regimen, and can be determined by one of skill in the art. The dosage can be adjusted by the individual physician in the event of any counterindications. Dosage can vary, and can be administered in one or more dose administrations daily, for one or several days. Guidance can be found in the literature for appropriate dosages for given classes of pharmaceutical products. A typical daily dosage of the disclosed composition used alone might range from about 1 µg/kg to up to 100 mg/kg of body weight or more per day, depending on the factors mentioned above.

In some embodiments, the molecule containing lenalidomide is administered in a dose equivalent to parenteral administration of about 0.1 ng to about 100 g per kg of body weight, about 10 ng to about 50 g per kg of body weight, about 100 ng to about 1 g per kg of body weight, from about 1 µg to about 100 mg per kg of body weight, from about 1 µg to about 50 mg per kg of body weight, from about 1 mg to about 500 mg per kg of body weight; and from about 1 mg to about 50 mg per kg of body weight. Alternatively, the amount of molecule containing lenalidomide administered to achieve a therapeutic effective dose is about 0.1 ng, 1 ng, 10 ng, 100 ng, 1 µg, 10 µg, 100 µg, 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 30 mg, 40 mg, 50 mg, 60 mg, 70 mg, 80 mg, 90 mg, 100 mg, 500 mg per kg of body weight or greater.

Definitions

The term "subject" refers to any individual who is the target of administration or treatment. The subject can be a vertebrate, for example, a mammal. Thus, the subject can be a human or veterinary patient. The term "patient" refers to a subject under the treatment of a clinician, e.g., physician.

The term "therapeutically effective" refers to the amount of the composition used is of sufficient quantity to ameliorate one or more causes or symptoms of a disease or disorder. Such amelioration only requires a reduction or alteration, not necessarily elimination.

The term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio.

The term "carrier" means a compound, composition, substance, or structure that, when in combination with a compound or composition, aids or facilitates preparation, storage, administration, delivery, effectiveness, selectivity, or any other feature of the compound or composition for its intended use or purpose. For example, a carrier can be selected to minimize any degradation of the active ingredient and to minimize any adverse side effects in the subject.

The term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

As used herein, "alkyl" is intended to include both branched and straight-chain saturated aliphatic hydrocarbon groups having the specified number of carbon atoms. Thus, $C_1$-$C_n$ as in "$C_1$-$C_6$ alkyl" is defined to include groups having 1, 2, n–1 or n carbons in a linear or branched arrangement, and specifically includes methyl, ethyl, propyl, butyl, pentyl, hexyl, and so on. An embodiment can be $C_1$-$C_{12}$ alkyl. "Alkoxy" represents an alkyl group as described above attached through an oxygen bridge.

The term "alkenyl" refers to a non-aromatic hydrocarbon radical, straight or branched, containing at least 1 carbon to carbon double bond, and up to the maximum possible number of non-aromatic carbon-carbon double bonds may be present. Thus, $C_2$-$C_6$ alkenyl is defined to include groups having 1, 2 . . . , n–1 or n carbons. For example, "$C_2$-$C_6$ alkenyl" means an alkenyl radical having 2, 3, 4, 5, or 6 carbon atoms, and at least 1 carbon-carbon double bond, and up to, for example, 3 carbon-carbon double bonds in the case of a $C_6$ alkenyl, respectively. Alkenyl groups include ethenyl, propenyl, butenyl and cyclohexenyl. As described above with respect to alkyl, the straight, branched or cyclic portion of the alkenyl group may contain double bonds and may be substituted if a substituted alkenyl group is indicated. An embodiment can be $C_2$-$C_{12}$ alkenyl.

The term "alkynyl" refers to a hydrocarbon radical straight or branched, containing at least 1 carbon to carbon triple bond, and up to the maximum possible number of non-aromatic carbon-carbon triple bonds may be present. Thus, $C_2$-$C_n$ alkynyl is defined to include groups having 1, 2 . . . , n–1 or n carbons. For example, "$C_2$-$C_6$ alkynyl" means an alkynyl radical having 2 or 3 carbon atoms, and 1 carbon-carbon triple bond, or having 4 or 5 carbon atoms, and up to 2 carbon-carbon triple bonds, or having 6 carbon atoms, and up to 3 carbon-carbon triple bonds. Alkynyl groups include ethynyl, propynyl and butynyl. As described above with respect to alkyl, the straight or branched portion of the alkynyl group may contain triple bonds and may be substituted if a substituted alkynyl group is indicated. An embodiment can be a $C_2$-$C_n$ alkynyl.

As used herein, "aryl" is intended to mean any stable monocyclic or bicyclic carbon ring of up to 10 atoms in each ring, wherein at least one ring is aromatic. Examples of such aryl elements include phenyl, naphthyl, tetrahydro-naphthyl, indanyl, biphenyl, phenanthryl, anthryl or acenaphthyl. In cases where the aryl substituent is bicyclic and one ring is non-aromatic, it is understood that attachment is via the aromatic ring. The substituted aryls included in this invention include substitution at any suitable position with amines, substituted amines, alkylamines, hydroxys and alkylhydroxys, wherein the "alkyl" portion of the alkylamines and alkylhydroxys is a $C_2$-$C_n$ alkyl as defined hereinabove. The substituted amines may be substituted with alkyl, alkenyl, alkynl, or aryl groups as hereinabove defined.

The alkyl, alkenyl, alkynyl, and aryl substituents may be substituted or unsubstituted, unless specifically defined otherwise. For example, a ($C_1$-$C_6$) alkyl may be substituted with one or more substituents selected from OH, oxo, halogen, alkoxy, dialkylamino, or heterocyclyl, such as morpholinyl, piperidinyl.

In the disclosed compounds, alkyl, alkenyl, and alkynyl groups can be further substituted by replacing one or more=hydrogen atoms by non-hydrogen groups described herein to the extent possible. These include, but are not limited to, halo, hydroxy, mercapto, amino, carboxy, cyano and carbamoyl.

The term "substituted" as used herein means that a given structure has a substituent which can be an alkyl, alkenyl, or aryl group as defined above. The term shall be deemed to include multiple degrees of substitution by a named substitutent. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

It is understood that substituents and substitution patterns on the disclosed compounds can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results.

As used herein, "administering" an agent may be performed using any of the various methods or delivery systems well known to those skilled in the art. The administering can be performed, for example, orally, parenterally, intraperitoneally, intravenously, intraarterially, transdermally, sublingually, intramuscularly, rectally, transbuccally, intranasally, liposomally, via inhalation, vaginally, intraoccularly, via local delivery, subcutaneously, intraadiposally, intraarticularly, intrathecally, into a cerebral ventricle, intraventicularly, intratumorally, into cerebral parenchyma or intraparenchchymally. The following delivery systems, which employ a number of routinely used pharmaceutical carriers, may be used but are only representative of the many possible systems envisioned for administering compositions in accordance with the invention.

As used herein, "pharmaceutically acceptable carrier" refers to a carrier or excipient that is suitable for use with humans and/or animals without undue adverse side effects (such as toxicity, irritation, and allergic response) commensurate with a reasonable benefit/risk ratio. it can be a pharmaceutically acceptable solvent, suspending agent or vehicle, for delivering the instant compounds to the subject.

The disclosed compounds may be in a salt form. As used herein, a "salt" is a salt of the instant compounds which has been modified by making acid or base salts of the compounds. In the case of compounds used to treat an infection or disease, the salt is pharmaceutically acceptable. Examples of pharmaceutically acceptable salts include, but are not limited to, mineral or organic acid salts of basic residues such as amines; alkali or organic salts of acidic residues such as phenols. The salts can be made using an organic or inorganic acid. Such acid salts are chlorides, bromides, sulfates, nitrates, phosphates, sulfonates, formates, tartrates, maleates, malates, citrates, benzoates, salicylates, ascorbates, and the like. Phenolate salts are the alkaline earth metal salts, sodium, potassium or lithium. The term "pharmaceutically acceptable salt" in this respect, refers to the relatively non-toxic, inorganic and organic acid or base addition salts of compounds of the present invention. These salts can be prepared in situ during the final isolation and purification of the compounds of the invention, or by separately reacting a purified compound of the invention in its free base or free acid form with a suitable organic or inorganic acid or base, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like.

As used herein, the term "therapeutically effective amount" or "effective amount" refers to the quantity of a component that is sufficient to yield a desired therapeutic response without undue adverse side effects (such as toxicity, irritation, or allergic response) commensurate with a reasonable benefit/risk ratio when used in the manner of this invention. The specific effective amount will vary with such factors as the particular condition being treated, the physical condition of the patient, the type of mammal being treated, the duration of the treatment, the nature of concurrent therapy (if any), and the specific formulations employed and the structure of the compounds or its derivatives.

A number of embodiments of the invention have been described. Nevertheless, it will be understood that various modifications may be made without departing from the spirit and scope of the invention. Accordingly, other embodiments are within the scope of the following claims.

EXAMPLES

Example 1: In Vitro Evaluation of LB-100 on Lymphoblastoid Cells

Results

Cell Cycle

Figure 2:
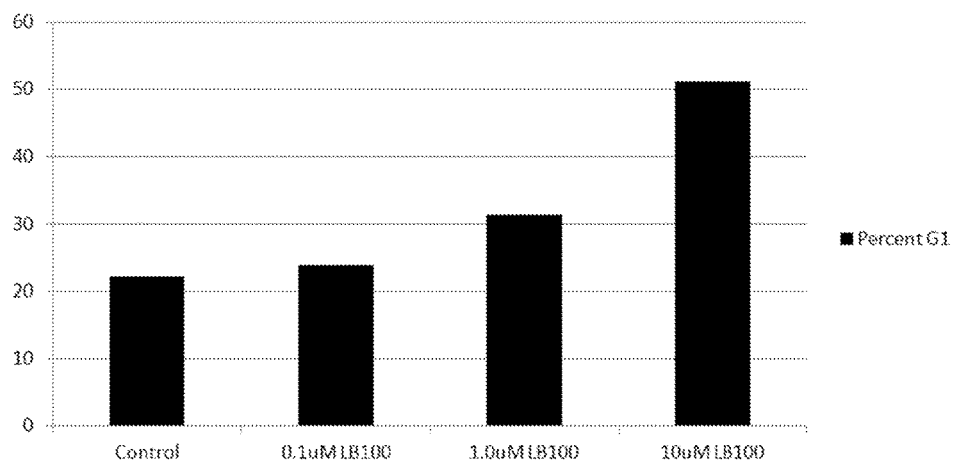
FIG. 2 is a bar graph showing percent of Namalwa cells in G1 arrest 24 hours after treatment with 0.1 µM, 1.0 µM or 10 µM LB-100 compared to control.

Namalwa cells were treated with LB-100 dissolved in DMSO or MSG LB-100 treatment led to G1 arrest at 1 and 10 µM in MSG and at 10 µM in DMSO (Table 1 and FIG. 1). LB-100 treatment led to G1 arrest in a dose-dependent fashion (Table 2 and FIG. 2).

TABLE 1

|  | G1 | G2/M | S |
| --- | --- | --- | --- |
| DMSO |  |  |  |
| Control | 16.93 | 21.17 | 61.9 |
| Vehicle | 18.97 | 19.59 | 61.44 |
| 0.1 µM LB100 | 17.73 | 16.51 | 65.76 |
| 1.0 µM LB100 | 18.38 | 18.22 | 63.41 |
| 10 µM LB100 | 28.97 | 8.9 | 62.13 |
| MSG |  |  |  |
| Control | 17.78 | 19.96 | 62.26 |
| Vehicle | 18.05 | 19.57 | 62.38 |
| 0.1 uM LB100 | 18.69 | 17.93 | 63.37 |
| 1.0 uM LB100 | 41.48 | 6.96 | 51.56 |
| 10 uM LB100 | 46.34 | 8.5 | 45.15 |

TABLE 2

|  | Percent G1 | S | G2/M |
| --- | --- | --- | --- |
| Control | 22.32 | 61.23 | 16.42 |
| 0.1 µM LB100 | 24.01 | 63.93 | 12.06 |
| 1.0 µM LB100 | 31.35 | 47.85 | 20.8 |
| 10 µM LB100 | 51.18 | 42.69 | 6.13 |

Apoptosis—Cell Lines

Figure 3:
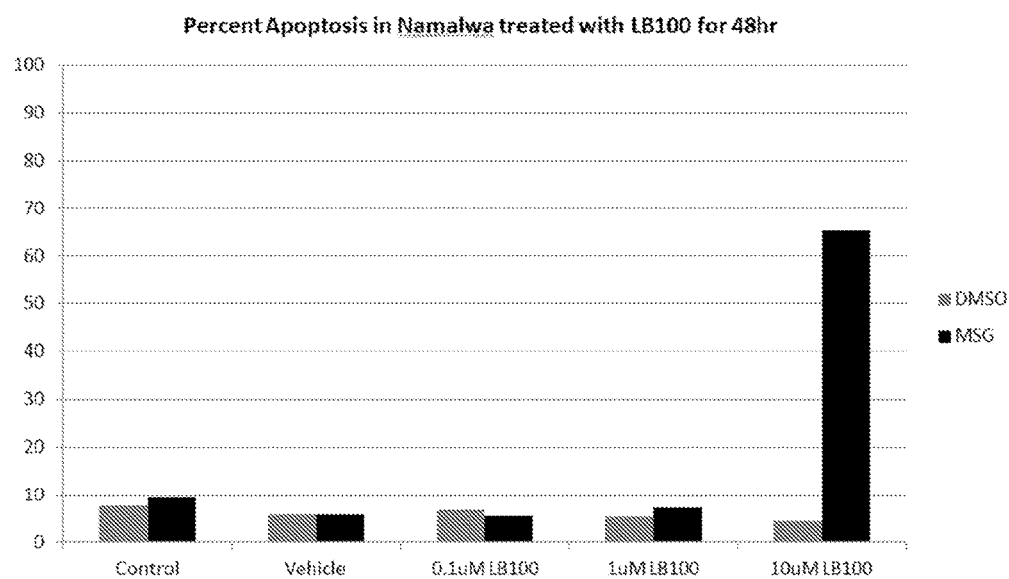
FIG. 3 is a bar graph showing percentage of Namalwa cells undergoing apoptosis after treatment with 0.1 µM, 1.0 µM or 10 µM LB-100 dissolved in DMSO (grey) or MSG (black) compared to control and vehicle.
Figure 4A:
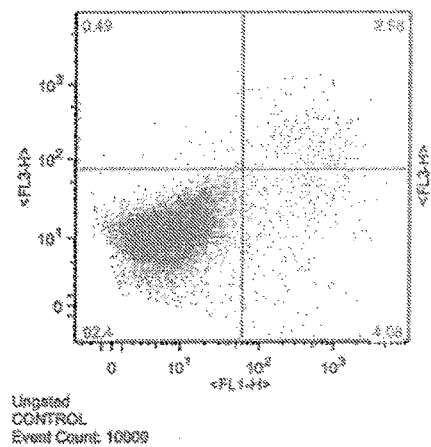
FIGS. 4A to 4D are a series of flow cytometry plots showing percentage of Namalwa cells undergoing apoptosis after treatment with control (FIG. 4A), 0.1 µM (FIG. 4B), 1.0 µM (FIG. 4C), or 10 µM (FIG. 4D) LB-100.
Figure 4B:
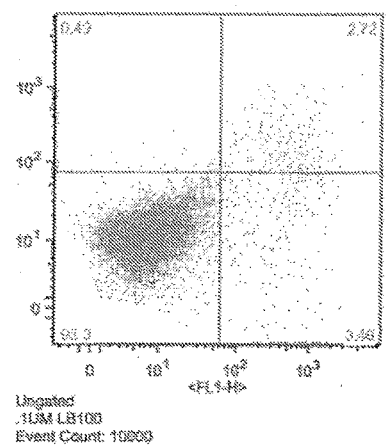
Figure 4C:
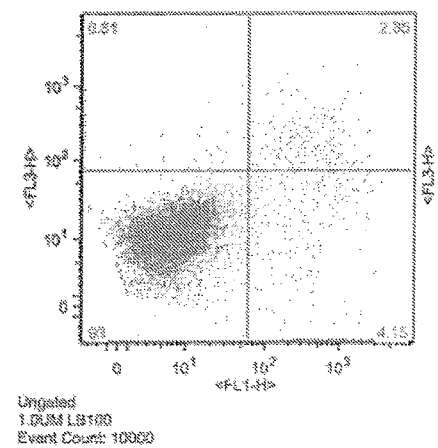
Figure 4D:
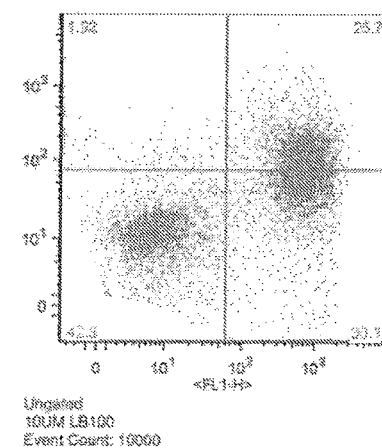

LB-100 treatment of Namalwa cell led to apoptosis at 10 µM when dissolved in MSG (FIGS. 3 and 4 and Table 3).

TABLE 3

| Treatment | Percent Apoptosis |
| --- | --- |
| CONTROL | 7.06 |
| 0.1 µM LB100 | 6.18 |
| 1.0 µM LB100 | 6.5 |
| 10 µM LB100 | 55.8 |

Apoptosis—Patient Cells, 5q Vs Non-5q

Figure 5:
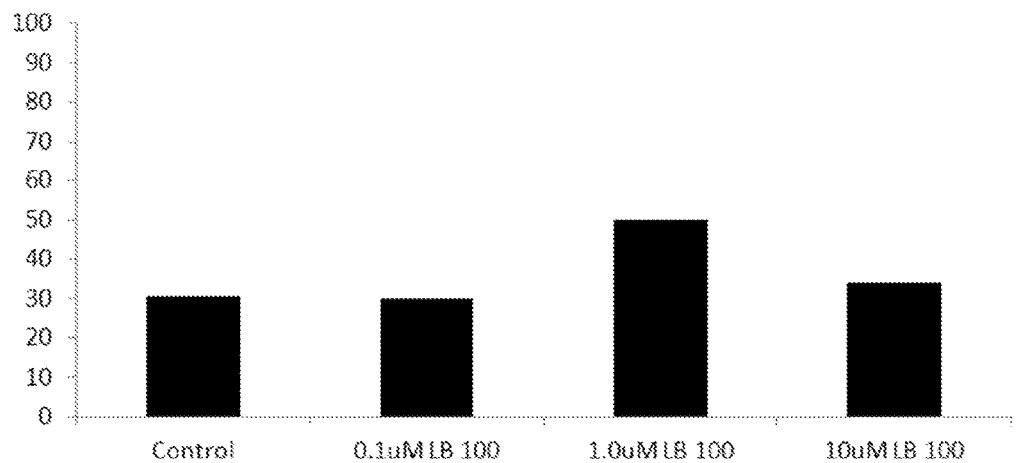
FIG. 5 is a bar graph showing percentage of primary BM MNCs from a Del(5q) patient undergoing apoptosis after treatment with 0.1 µM, 1.0 µM or 10 µM LB-100, compared to a control.
Figure 6:
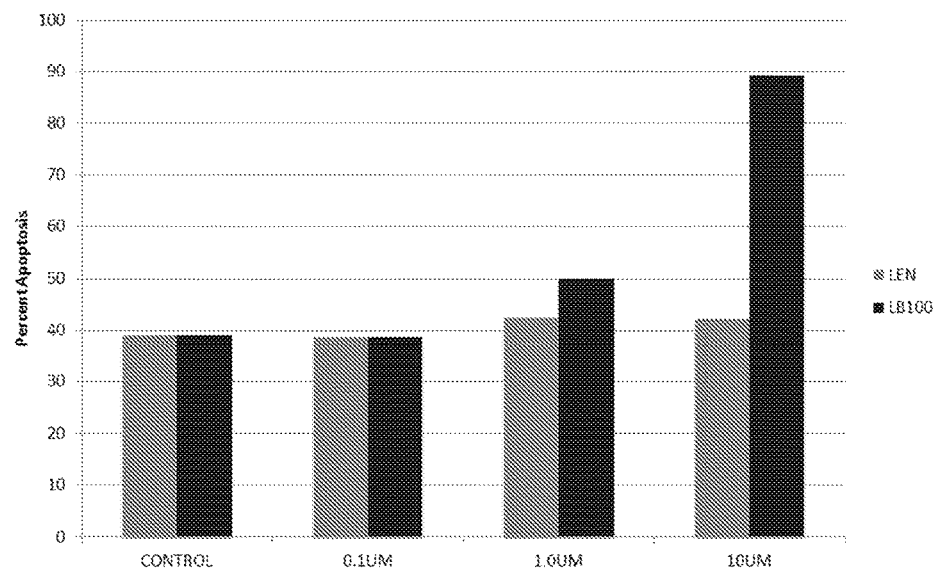
FIG. 6 is a bar graph showing percentage of primary BM MNCs from a Del(5q) patient undergoing apoptosis after treatment with 0.1 µM, 1.0 µM, or 10 µM lenalidomide (grey) or 0.1 µM, 1.0 µM, or 10 µM LB-100 (black), compared to a control.

Non-del(5q) patient BM MNCs treated with LB-100 did not lead to apoptosis (FIG. 5). For del(5q) patient BM MNCs, LB-100 induced apoptosis in a dose dependent fashion and was more cytotoxic than lenalidomide at 10 µM and with a mild increase in apoptosis at 1 µM (FIG. 6)

MTT Assays

Figure 7A:
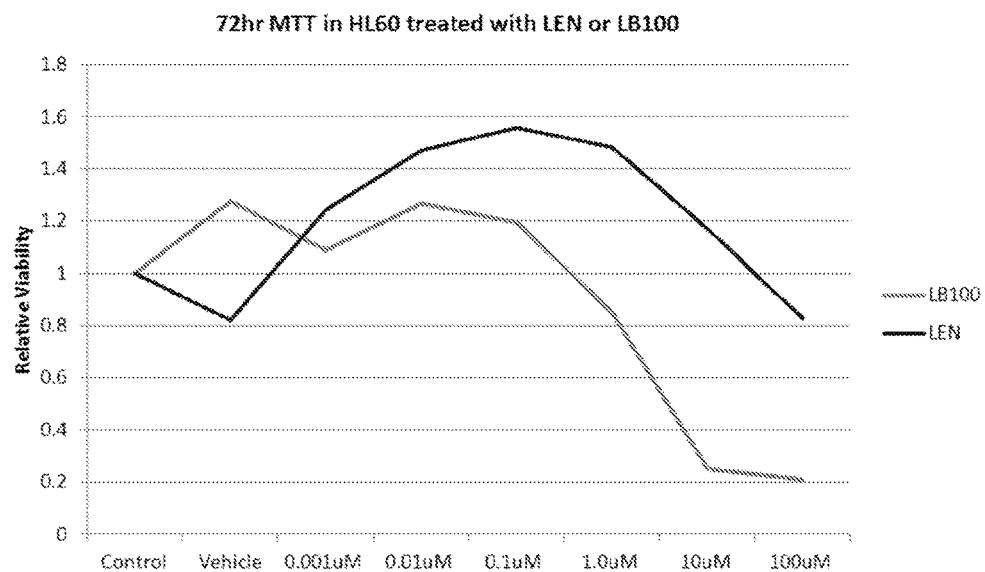
FIG. 7A is a graph showing proliferation of HL60 cells 72 hours after treatment with 0.001 µM, 0.01 µM, 0.1 µM, 1.0 µM, 10 µM, or 100 µM LB-100 (grey) or 0.001 µM, 0.01 µM, 0.1 µM, 1.0 µM, 10 µM, or 100 µM lenalidomide (black), compared to control or vehicle.
Figure 7B:
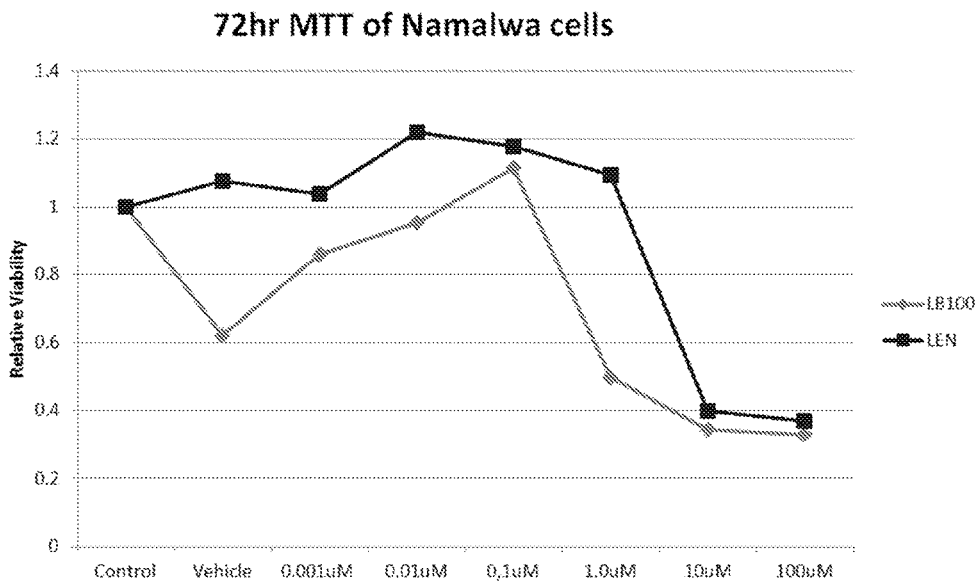
FIGS. 7B to 7C are graphs showing proliferation of Namalwa cells 72 hours after treatment with 0.001 µM, 0.01 µM, 0.1 µM, 1.0 µM, 10 µM, or 100 µM LB-100 (♦), 0.001 µM, 0.01 µM, 0.1 µM, 1.0 µM, 10 µM, or 100 µM lenalidomide (■), or 0.001 µM, 0.01 µM, 0.1 µM, 1.0 µM, 10 µM, or 100 µM cantharidin (Δ), compared to control or vehicle.
Figure 7C:
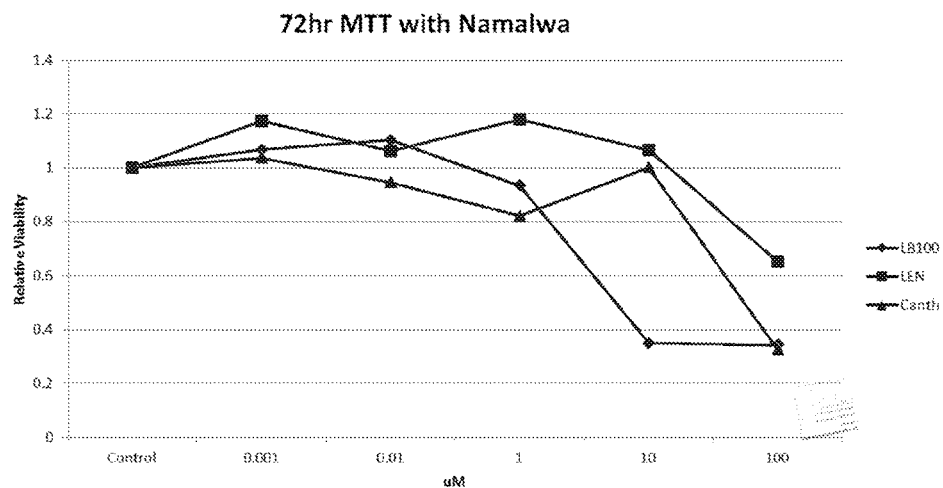
Figure 8A:
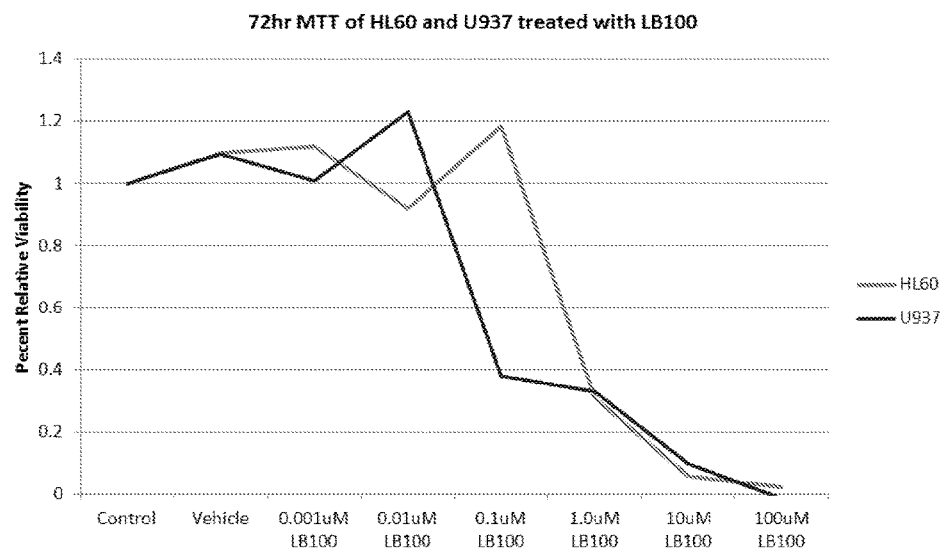
FIGS. 8A and 8B are graphs showing proliferation of HL60 cells (grey) or U937 cells (black) 72 hours after treatment with 001 µM, 0.01 µM, 0.1 µM, 1.0 µM, 10 µM, or 100 µM LB-100.
Figure 8B:
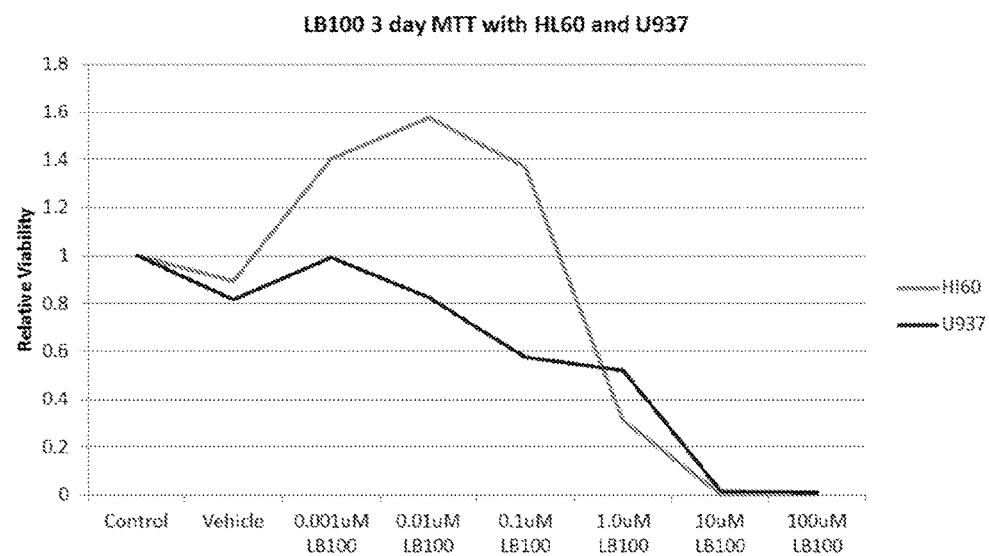
Figure 9:
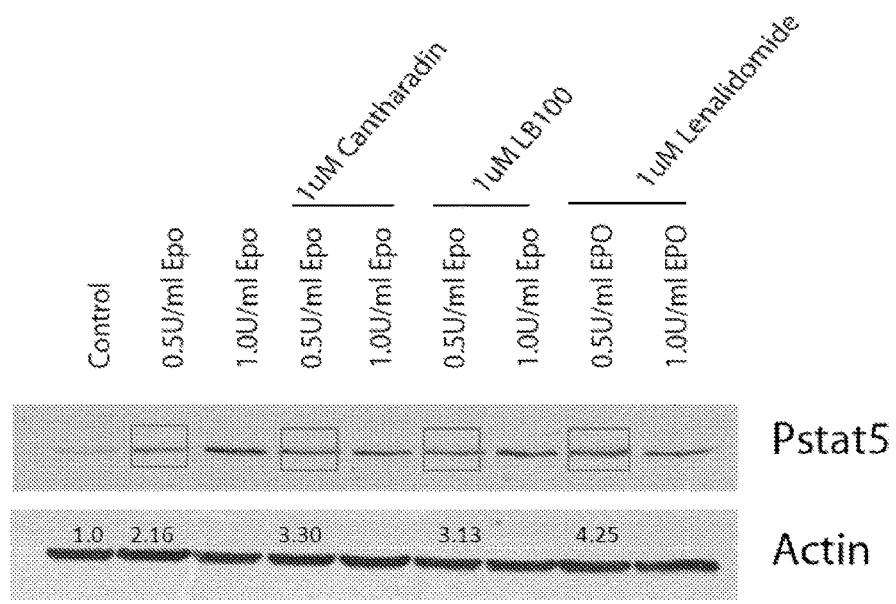
FIG. 9 is a western blot showing Pstat5 expression after treatment with 1 µM cantharidin, 1 µM LB100, or 1 µM lenalidomide and either 0.5 or 1.0 U·ml Epo.

HL60 cells treated with LB-100 showed a significant decreased proliferation in comparison to treatment with lenalidomide, with a significant difference at 1 µM (FIG. 7A). HL60 cells and U937 cells were compared (FIGS. 8A and 8B). Namalwa cells treated with LB-100 showed a significant decrease in proliferation in comparison to control (FIGS. 7B and 7C).

Example 2: A Phase 1 Study Evaluating the Safety and Efficacy of LB-100 in Patients with Low or Intermediate-1 Risk Myelodysplastic Syndrome LB-100 is a specific small molecule inhibitor of PP2A that displays greater potency than lenalidomide. LB-100 has been shown in vitro and in vivo to cause cell cycle arrest in several malignancies and also sensitizes cells to chemotherapy and radiation. The safety, tolerance and preliminary activity of targeted PP2A inhibition by LB100 is investigated in lower risk MDS patients with symptomatic anemia.

Patients with low or intermediate-1 risk MDS stratified by International Prognostic Scoring System (IPSS) with symptomatic anemia receiving LB-100 intravenously are examined. The primary objective of this study is to determine the safety profile and the maximum tolerated dose (MTD) of LB-100 as determined by dose-limiting toxicities (DLTs), and to characterize the plasma pharmacokinetics (PK) of LB-100. Secondary objectives include exploration of preliminary estimates of LB-100 activity using standard international working group (IWG) 2006 response criteria, evaluation of LB-100 activity as measured by rise in hemoglobin or frequency of red blood cell (RBC) transfusions, rate of TI and the durability of response, assessment of the effect of LB-100 on pathologic and cytogenetic responses, and evaluation of the effect of LB-100 on the hematologic and cytogenetic response in patients with del(5q) MDS.

Study Endpoints:

Primary Endpoints include safety, MDT, and pharmacokinetics. These include incidence and severity of adverse events (AEs), graded according to the National Cancer, Institute Common Terminology Criteria for Adverse Events (NCI CTCAE), Version 3.0, MTD based on the protocol defined DLT, and exposure-related PK parameters generated from LB-100 plasma concentration-time data using standard PK analysis approaches Secondary Endpoints include efficacy as defined by the IWG criteria, erythroid hematological improvement (HI-E), cytogenetic response, response (complete response [CR], partial response [PR] and marrow CR), response (in subset of patients with del(5q) MDS who have failed lenalidomide, platelet hematological improvement (HI-P), neutrophil hematological improvement (HI-N), duration of response, and Acute myeloid leukemia (AML) transformation according to World Health Organization (WHO) criteria.

Study Design

This is a Phase 1 open-label study, conducted in 2 phases: a Dose Escalation Phase followed by an Expansion Phase. The initial Dose Escalation Phase evaluates LB-100 administered intravenously. Cohorts of at least 3 evaluable patients are enrolled using a modified 3+3 design. In the Dose Escalation Phase, patients receive intravenous infusions of LB-100 over 30 minutes on days 1-3 of each 21 day cycle at escalating doses starting at Dose Level 1 (0.5 mg/m$^2$). Patients are followed for at least 3 weeks before the safety of each cohort can be fully assessed and decisions made for dose escalation in the next cohort. The MTD is defined as the dose level below which DLT is manifested in ≥33% of the patients.

Following completion of the Dose Escalation Phase, LB-100 administered intravenously is evaluated in the Expansion Phase, in which up to 14 additional evaluable patients are treated at the MTD using the 21 day cycle.

The number of patients enrolled depends on the number of dose levels evaluated before reaching DLT. Three to 6 evaluable patients are entered per dose level for each schedule. Up to 60 evaluable patients are treated in the Dose Escalation Phase. Up to 14 additional evaluable patients are treated at the level of the MTD of one or more of the schedules in the Expansion Phase, for a total of up to 20 evaluable patients at the MTD.

Correlative Studies include assessing target inhibition and the biological activity of PP2A inhibition by evaluating changes in phosphorylation of PP2A substrates (e.g., CDC25C, MDM2) and p53 expression by immunohistochemistry in bone marrow (BM) biopsies. Also included is evaluation of changes in BM progenitor colony forming capacity, comparison of changes in erythropoietin-induced STAT5 activation in erythroid progenitors by flow cytometry in the presence of human plasma before and after LB100 treatment, and assessment of possible PK/pharmacodynamic (PD) or PD/efficacy correlations.

Example 3. Additional Studies Evaluating the Efficacy of LB-100

Additional studies, similar to the aforementioned Phase I design, are conducted to evaluate the efficacy of LB-100, alone or in combination with lenalidomide, in patients with del(5q) MDS or non-del(5q) MDS.

An amount of LB-100 is administered to a subject afflicted with del(5q) MDS. The amount of the LB-100 is effective to treat the del(5q) MDS. An amount of LB-100 in combination with lenalidomide is administered to a subject afflicted with del(5q) MDS. The amount of the LB-100 and the lenalidomide is effective to treat the del(5q) MDS.

An amount of LB-100 is administered to a subject afflicted with non-del(5q) MDS. The amount of the LB-100 is effective to treat the non-del(5q) MDS. An amount of LB-100 in combination with lenalidomide is administered to a subject afflicted with non-del(5q) MDS. The amount of the LB-100 and the lenalidomide is effective to treat the non-del(5q) MDS.

In each of the above studies, MDS that is resistant to lenalidomide is also evaluated and the LB-100 or the LB-100 in combination with lenalidomide is effective to treat the MDS.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A method for treating myelodysplastic syndrome (MDS) in a subject afflicted therewith, comprising administering to the subject a therapeutically effective amount of a protein phosphatase 2A (PP2A) inhibitor; wherein the PP2A inhibitor is a compound having the structure:

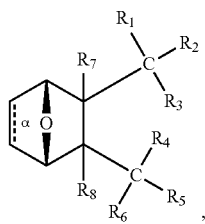

wherein
bond α is present or absent
$R_1$ and $R_2$ together are =O;
$R_3$ is OH, O⁻, $OR_9$, $O(CH_2)_{1-6}R_9$, SH, S⁻, or $SR_9$, wherein $R_9$ is H, alkyl, alkenyl, alkynyl or aryl;
$R_4$ is

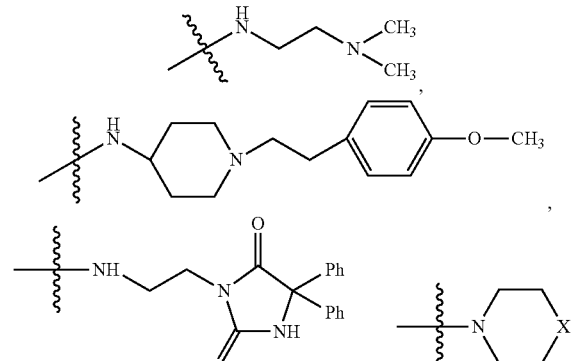

where X is O, S, $NR_{10}$, $N^+HR_{10}$ or $N^+R_{10}R_{10}$,
where each $R_{10}$ is independently H, alkyl, alkenyl, alkynyl, aryl,

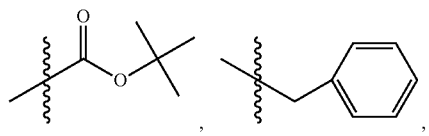

—$CH_2CN$, $CH_2CO_2R_{11}$, or $CH_2COR_{11}$,
wherein each $R_{11}$ is independently H, alkyl, alkenyl or alkynyl;
$R_5$ and $R_6$ taken together are =O;
$R_7$ and $R_8$ are each H,
or a pharmaceutically acceptable salt, zwitterion, or ester thereof.

2. The method of claim 1, wherein the MDS in the subject is del(5q) MDS.
3. The method of claim 1, wherein the MDS in the subject is non-del(5q) MDS or unclassified myelodysplastic syndrome (MDS-U).
4. The method of claim 3, wherein the MDS is characterized by refractory anemia (RA), refractory neutropenia (RN), refractory thrombocytopenia (RT), refractory anemia (RA) with ringed sideroblasts (RARS), refractory cytopenia with multilineage dysplasia (RCMD), refractory cytopenia with multilineage dysplasia and ringed sideroblasts (RCMD-RS), refractory anemia (RA) with excess blasts-1 (RAEB-1), refractory anemia (RA) with excess blasts-2 (RAEB-2) or refractory anemia (RA) with excess Blasts in Transformation (RAEB-t), or a combination thereof.
5. The method of claim 1, wherein the MDS has become resistant to a current therapy, wherein the current therapy comprises treatment with lenalidomide, azacitidine or decitabine.
6. The method of claim 1, further comprising administering to the subject a therapeutically effective amount of lenalidomide (LEN) or dexamethasone.
7. The method of claim 5, wherein the PP2A inhibitor reduces or reverses the resistance of the MDS to the lenalidomide, or re-sensitizes the MDS to the lenalidomide.
8. A method for treating a myelodysplastic syndrome (MDS) in a subject, comprising administering to the subject an effective amount of
 (a) a first composition comprising lenalidomide, or a pharmaceutically acceptable salt thereof; and
 (b) a second composition comprising a protein phosphatase 2A (PP2A) inhibitor; wherein the PP2A inhibitor is a compound having the structure:

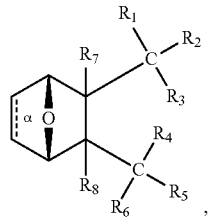

wherein
bond α is present or absent;
$R_1$ and $R_2$ together are =O;
$R_3$ is OH, O⁻, $OR_9$, $O(CH_2)_{1-6}R_9$, SH, S⁻, or $SR_9$, wherein $R_9$ is H, alkyl, alkenyl, alkynyl or aryl;
$R_4$ is

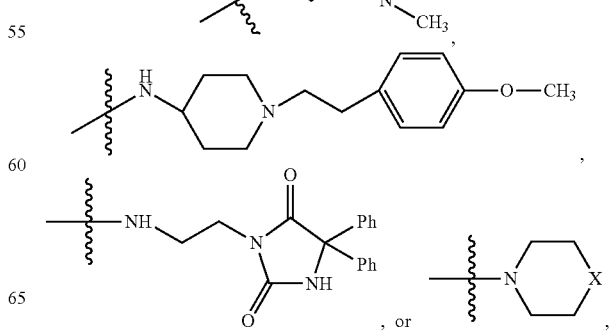

where X is O, S, $NR_{10}$, $N^+R_{10}$ or $N^+R_{10}R_{10}$,
where each $R_{10}$ is independently H, alkyl, alkenyl, alkynyl, aryl,

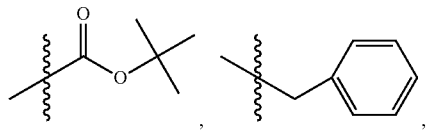

—$CH_2CN$, —$CH_2CO_2R_{11}$, or —$CH_2COR_{11}$,
wherein each $R_{11}$ is independently H, alkyl, alkenyl or alkynyl;

$R_5$ and $R_6$ taken together are =O;

$R_7$ and $R_8$ are each H, or a pharmaceutically acceptable salt, zwitterion, or ester thereof.

9. The method of claim 1, wherein the treating further comprises reducing the number of blasts in the bone marrow or peripheral blood of the subject, or reducing the number of myeloblasts in the bone marrow or peripheral blood of the subject, or reducing the number of sideroblasts or ringed sideroblasts in the bone marrow or peripheral blood of the subject, or increasing the concentration of normal red blood cells, normal white blood cells and/or platelets in the subject, or increasing the concentration of hemoglobin in the subject.

10. The method of claim 1, wherein the MDS in the subject is low risk MDS based on the IPSS system, intermediate-1 risk MDS based on the IPSS system, intermediate-2 risk MDS based on the IPSS system or high risk MDS based on the IPSS system.

11. The method of claim 1, wherein bond α in the compound is absent.

12. The method of claim 1, wherein the compound has the structure

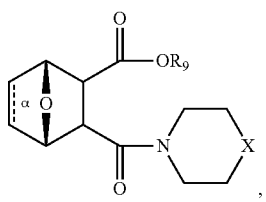

wherein
bond α is present or absent;
$R_9$ is present or absent and when present is H, alkyl, alkenyl, alkynyl or phenyl; and
X is O, $NR_{10}$, $NH^+R_{10}$ or $N^+R_{10}R_{10}$,
where each $R_{10}$ is independently H, alkyl, substituted alkyl, alkenyl, substituted alkenyl, alkynyl, substituted alkynyl, aryl,

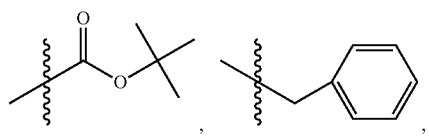

$CH_2CN$, —$CH_2CO_2R_{12}$, or —$CH_2COR_{12}$,
where $R_{12}$ is H or alkyl,
or a pharmaceutically acceptable salt, zwitterion or ester thereof.

13. The method of claim 1, wherein the compound has the structure

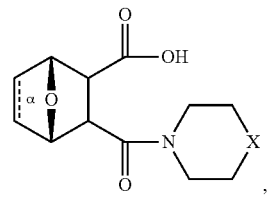

wherein
bond α is present or absent;
X is O or $NR_{10}$,
where each $R_{10}$ is independently H, alkyl, substituted alkyl, alkenyl, substituted alkenyl, alkynyl, substituted alkynyl, aryl,

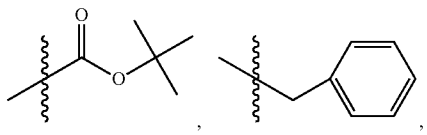

—$CH_2CN$, —$CH_2CO_2R_{12}$, or —$CH_2COR_{12}$,
where Rig is H or alkyl,
or a pharmaceutically acceptable salt, zwitterion or ester thereof, or has the structure

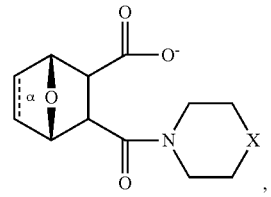

wherein
bond α is present or absent;
X is O or $NH^+R_{10}$,
where $R_{10}$ is H, alkyl, substituted alkyl, alkenyl, substituted alkenyl, alkynyl, substituted alkynyl, aryl,

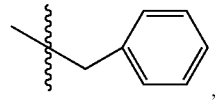 [SMILES: *Cc1ccccc1]

—$CH_2CN$, —$CH_2CO_2R_{12}$, or —$CH_2COR_{12}$,
where $R_{12}$ is H or alkyl,
or a pharmaceutically acceptable salt, zwitterion or ester thereof.

14. The method of claim 1, wherein the compound has the structure

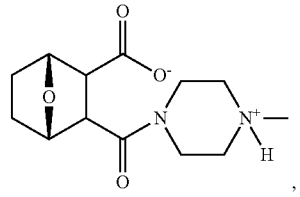

or a pharmaceutically acceptable salt or ester thereof.

15. The method of claim 1, wherein the compound has the structure

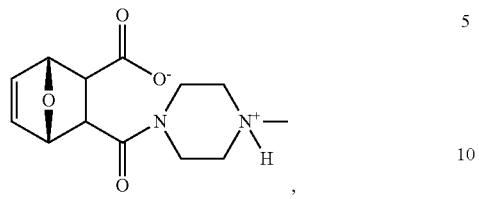

or a pharmaceutically acceptable salt or ester thereof.

16. The method of claim 1, wherein the compound is contained in a pharmaceutical composition comprising monosodium glutamate.

17. The method of claim 14, wherein the compound is contained in a pharmaceutical composition comprising monosodium glutamate.

18. The method of claim 16, wherein the treating further comprises inducing apoptosis of abnormal bone marrow cells, inducing apoptosis of at least 50% of abnormal bone marrow cells or inducing G1 cell arrest in at least 30% of abnormal bone marrow cells.

19. The method of claim 17, wherein the treating further comprises inducing apoptosis of abnormal bone marrow cells, inducing apoptosis of at least 50% of abnormal bone marrow cells or inducing G1 cell arrest in at least 30% of abnormal bone marrow cells.

* * * * *